(12) United States Patent
Jaramillo et al.

(10) Patent No.: US 8,888,791 B2
(45) Date of Patent: *Nov. 18, 2014

(54) SURGICAL INSTRUMENT AND METHOD FOR TENSIONING AND SECURING A FLEXIBLE SUTURE

(75) Inventors: Jorge Jaramillo, Burnaby (CA); Doug Goertzen, New Westminster (CA); Kevin Chaplin, Vancouver (CA); Dan Gelbart, Vancouver (CA); Ian Garben, Burnaby (CA); Monica Spisar, Vancouver (CA)

(73) Assignee: Kardium Inc., Burnaby (CA)

( * ) Notice: Subject to any disclaimer, the term of this patent is extended or adjusted under 35 U.S.C. 154(b) by 1254 days.

This patent is subject to a terminal disclaimer.

(21) Appl. No.: 12/436,926

(22) Filed: May 7, 2009

(65) Prior Publication Data

US 2010/0087837 A1 Apr. 8, 2010

Related U.S. Application Data

(63) Continuation-in-part of application No. 12/246,614, filed on Oct. 7, 2008.

(51) Int. Cl.
*A61B 17/10* (2006.01)
*A61B 17/88* (2006.01)
*A61B 17/04* (2006.01)
*A61B 19/00* (2006.01)
*A61B 17/82* (2006.01)

(52) U.S. Cl.
CPC ............ *A61B 17/04* (2013.01); *A61B 17/0467* (2013.01); *A61B 2019/464* (2013.01); *A61B 2017/0496* (2013.01); *A61B 2019/4836* (2013.01); *A61B 17/8861* (2013.01); *A61B 17/8869* (2013.01); *A61B 17/823* (2013.01)
USPC ............ 606/139; 606/103; 606/144; 606/148

(58) Field of Classification Search
USPC ............................ 606/103, 139–150, 74, 113
See application file for complete search history.

(56) References Cited

U.S. PATENT DOCUMENTS 3,959,960 A 6/1976 Santos
4,527,554 A * 7/1985 Klein ............................ 606/103

(Continued)

FOREIGN PATENT DOCUMENTS

WO 2007/115390 10/2007
WO 2008/073947 A2 6/2008

OTHER PUBLICATIONS

International Search Report, mailed Sep. 10, 2010, for PCT/US2010/021835, 4 pages.

(Continued)

*Primary Examiner* — Jerry Cumberledge
*Assistant Examiner* — Nicholas Plionis
(74) *Attorney, Agent, or Firm* — Rossi, Kimms & McDowell LLP

(57) ABSTRACT

A surgical instrument may be used to apply tension to a flexible suture to close and secure a broken or cut bone (e.g. a sternum following a sternotomy). The device preferably applies an adjustable tension to the flexible suture in order to secure the bone together. Multiple instruments may be used together to ensure the desired tension is applied to the entire bone structure being secured with the flexible sutures. Once the desired tension is achieved, the device preferably provides a mechanism to apply a uniform twist to the flexible suture to lock the flexible suture in place. The instrument preferably decreases the upward tension applied to the flexible sutures over the duration of the application of twisting. The device may automatically cut the flexible suture, or the flexible suture may be cut by the surgeon once the twisting action has been performed.

29 Claims, 22 Drawing Sheets

(56) References Cited

U.S. PATENT DOCUMENTS

| | | | | |
|---|---|---|---|---|
| 5,021,059 A | 6/1991 | Kensey et al. | | 606/213 |
| 5,100,418 A | 3/1992 | Yoon et al. | | 606/139 |
| 5,156,609 A | 10/1992 | Nakao et al. | | 606/142 |
| 5,320,632 A | 6/1994 | Heidmueller | | 606/144 |
| 5,364,408 A | 11/1994 | Gordon | | 606/144 |
| 5,366,459 A | 11/1994 | Yoon | | 606/151 |
| 5,368,601 A | 11/1994 | Sauer et al. | | 606/144 |
| 5,374,275 A | 12/1994 | Bradley et al. | | 606/144 |
| 5,417,698 A * | 5/1995 | Green et al. | | 606/139 |
| 5,478,353 A | 12/1995 | Yoon | | 606/213 |
| 5,690,649 A | 11/1997 | Li | | 606/139 |
| 5,728,114 A | 3/1998 | Evans et al. | | 606/148 |
| 5,782,861 A | 7/1998 | Cragg et al. | | 606/216 |
| 5,865,791 A | 2/1999 | Whayne et al. | | 604/49 |
| 5,919,207 A | 7/1999 | Taheri | | 606/219 |
| 5,961,440 A | 10/1999 | Schweich, Jr. et al. | | 600/16 |
| 5,971,994 A * | 10/1999 | Fritzsch | | 606/113 |
| 5,980,473 A * | 11/1999 | Korakianitis et al. | | 600/587 |
| 5,984,950 A | 11/1999 | Cragg et al. | | 606/216 |
| 6,113,610 A | 9/2000 | Poncet | | 606/139 |
| 6,241,747 B1 | 6/2001 | Ruff | | 606/216 |
| 6,248,124 B1 | 6/2001 | Pedros et al. | | 606/144 |
| 6,258,258 B1 | 7/2001 | Sartori et al. | | 208/263 |
| 6,358,258 B1 | 3/2002 | Arcia et al. | | 606/139 |
| 6,391,048 B1 | 5/2002 | Ginn et al. | | 606/213 |
| 6,432,115 B1 | 8/2002 | Mollenauer et al. | | 606/148 |
| 6,506,210 B1 | 1/2003 | Kanner | | 606/213 |
| 6,575,971 B2 | 6/2003 | Hauck et al. | | 606/52 |
| 6,626,930 B1 | 9/2003 | Allen et al. | | 606/213 |
| 6,676,685 B2 | 1/2004 | Pedros et al. | | 606/213 |
| 6,743,241 B2 | 6/2004 | Kerr | | 606/144 |
| 6,752,810 B1 * | 6/2004 | Gao et al. | | 606/103 |
| 6,960,229 B2 | 11/2005 | Mathis et al. | | 623/2.36 |
| 6,986,775 B2 | 1/2006 | Morales et al. | | 606/139 |
| 7,674,276 B2 * | 3/2010 | Stone et al. | | 606/232 |
| 2001/0003158 A1 | 6/2001 | Kensey et al. | | 606/213 |
| 2001/0005787 A1 | 6/2001 | Oz et al. | | 606/142 |
| 2003/0028202 A1 | 2/2003 | Sancoff et al. | | 606/144 |
| 2003/0208210 A1 | 11/2003 | Dreyfuss et al. | | 606/144 |
| 2004/0193187 A1 | 9/2004 | Boehringer et al. | | 606/144 |
| 2005/0055089 A1 | 3/2005 | Macoviak et al. | | 623/2.37 |
| 2005/0090840 A1 * | 4/2005 | Gerbino et al. | | 606/148 |
| 2005/0107871 A1 | 5/2005 | Realyvasquez et al. | | 623/2.11 |
| 2005/0125030 A1 | 6/2005 | Forsberg et al. | | 606/213 |
| 2005/0131441 A1 * | 6/2005 | Iio et al. | | 606/182 |
| 2005/0149014 A1 | 7/2005 | Hauck et al. | | 606/41 |
| 2005/0197694 A1 | 9/2005 | Pai et al. | | 623/2.1 |
| 2006/0015038 A1 | 1/2006 | Weymarn-Scharli | | 600/585 |
| 2006/0135968 A1 | 6/2006 | Schaller | | 606/144 |
| 2006/0135970 A1 | 6/2006 | Schaller | | 606/152 |
| 2006/0184242 A1 | 8/2006 | Lichtenstein | | 623/2.37 |
| 2007/0089617 A1 * | 4/2007 | Legtenberg et al. | | 100/2 |
| 2007/0198058 A1 | 8/2007 | Gelbart et al. | | 606/213 |
| 2007/0213578 A1 | 9/2007 | Khairkhahan et al. | | 600/16 |
| 2007/0225736 A1 | 9/2007 | Zeiner et al. | | 606/148 |
| 2008/0045778 A1 | 2/2008 | Lichtenstein et al. | | 600/16 |
| 2008/0269785 A1 | 10/2008 | Lampropoulos et al. | | 606/144 |
| 2008/0275477 A1 | 11/2008 | Sterrett et al. | | 606/148 |
| 2009/0287304 A1 | 11/2009 | Dahlgren et al. | | 623/2.37 |
| 2010/0087837 A1 | 4/2010 | Jaramillo et al. | | 606/144 |
| 2011/0087227 A1 * | 4/2011 | Mazur et al. | | 606/62 |

OTHER PUBLICATIONS

Written Opinion, mailed Sep. 10, 2010, for PCT/US2010/021835, 6 pages.

Lichtenstein et al., "System for Improving Diastolic Dysfunction," U.S. Appl. No. 11/497,309, filed Aug. 2, 2006, 13 pages.

Jaramillo et al., "Surgical Instrument and Method for Tensioning and Securing a Flexible Structure," Office Action mailed Dec. 13, 2010 for U.S. Appl. No. 12/246,614, 12 pages.

Jaramillo et al., "Surgical Instrument and Method for Tensioning and Securing a Flexible Structure," Amendment filed Mar. 14, 2011 for U.S. Appl. No. 12/246,614, 22 pages.

Jaramillo et al., "Surgical Instrument and Method for Tensioning and Securing a Flexible Structure," Office Action mailed May 27, 2011 for U.S. Appl. No. 12/246,614, 23 pages.

Jaramillo et al., "Surgical Instrument and Method for Tensioning and Securing a Flexible Structure," Amendment filed Jul. 26, 2011 for U.S. Appl. No. 12/246,614, 41 pages.

Extended European Search Report, dated Sep. 26, 2013, for Application No. 10772405.6, 6 pages.

* cited by examiner

SURGICAL INSTRUMENT AND METHOD FOR TENSIONING AND SECURING A FLEXIBLE SUTURE

BACKGROUND

1. Field

This disclosure is generally related to securing bones using a flexible suture and more particularly to surgical instruments suitable for securing the sternum with flexible sutures following a sternotomy.

2. Description of the Related Art

During an open heart procedure, the patient's sternum is cut in half lengthwise in a procedure called a median sternotomy. At the end of the surgery, the two halves are brought together and secured with standard surgical wire sutures. The wire sutures may be placed around or through the sternum, and tension may be applied to the wire sutures to bring the two separated parts of the sternum together. Once in place, with the desired tension, the wire suture is then twisted together on itself in a helical pattern to lock the wire suture in place and prevent separation, or dehiscence of the sternum. This is typically done using surgical pliers to tension and twist the wire sutures together, but other methods may be used.

Dehiscence of the sternum is a serious concern for patients, hospitals and surgeons, occurring in an estimated 2.5% of all sternotomies. The dehiscence delays healing, may be uncomfortable for the patient, and increases the likelihood of infection which typically requires additional surgery to treat.

While securing the sternum together with the wire sutures, the surgeon attempts to apply sufficient tension so that the sternum is held together and does not dehisce following surgery. The surgeon also attempts to twist the wire sutures uniformly so that the wire sutures do not become unlocked and loosen following surgery, which may allow the sternum to dehisce. The surgeon would also like to ensure that the wire sutures do not break while being tensioned and twisted. Should a wire suture break, it may require the surgeon to replace all the wire sutures that have previously been tensioned and twisted, and the sternum closure be started again.

Instruments and methods for attaching a wire suture to two parts of a bone to hold the bone together and apply a tension to the wire suture are well known in the prior art. Various methods for locking the tensioned wire suture are also described in the prior art, including ferrules, crimps or twisting. Various methods of threading the wire suture through, or around the sternum have also been described in the literature, and methods such as single loops, double loops, or figure of eight loops may be used by surgeons to secure the sternum.

BRIEF SUMMARY OF THE INVENTION

Various embodiments of surgical instruments and methods for providing a desired tension to a flexible suture, and providing a twist to said flexible suture while under the desired tension, are described herein. One example of a flexible suture is a stainless steel wire suture as used in a sternal closure after a median sternotomy.

At least one embodiment of a surgical instrument may be summarized as comprising a mechanism for tensioning a flexible suture encircling a bone, a second mechanism for applying a plurality of twists to a flexible suture used to secure a flexible suture to a bone while maintaining tension in said suture, and a base that supports the surgical instrument on a bone during tensioning of a flexible suture. The flexible suture may be a stainless steel wire suture.

The surgical instrument may further include a base that comprises an open slot and at least one moveable member to constrain a flexible suture in the slot. The base preferably does not rotate relative to the bone. The surgical instrument may additionally comprise a slot to allow cutting of a flexible suture by a tool or comprise a mechanism for cutting a flexible suture. The surgical instrument may restrict a second flexible suture from being tensioned with the same surgical instrument. The surgical instrument may remain in a locked position after tensioning a flexible suture and restrict a second flexible suture from being tensioned with the same surgical instrument. The surgical instrument may be attached to a flexible suture before the suture is moved proximate to or encircles the bone. The surgical instrument preferably tensions the flexible suture before securing the suture by twisting.

At least one embodiment of a surgical instrument may be summarized as comprising a mechanism for tensioning a flexible suture encircling a bone, a second mechanism for applying a plurality of twists to a flexible suture used to secure a flexible suture to a bone while maintaining tension in said suture, and a removable handle used to drive at least one of the mechanisms. The flexible suture may be a stainless steel wire suture.

The surgical instrument may further include a mechanism for tensioning which comprises a one way clutch that restricts the release of tension from a flexible suture after tension has been applied to the flexible suture.

The surgical instrument may further include a mechanism for tensioning comprising one or more springs which are compressed as a flexible suture is tensioned. The instrument may further provide an indication of the tension applied to the flexible suture. The surgical instrument may restrict a second flexible suture from being tensioned with the same surgical instrument. The surgical instrument may remain in a locked position after tensioning a first flexible suture and restrict a second flexible suture from being tensioned with the same tool.

At least one embodiment of a surgical instrument may be summarized as comprising a mechanism for tensioning a flexible suture encircling a bone where the mechanism for tensioning comprises at least one member for securing at least one end of a flexible suture, a second mechanism for applying a plurality of twists to a flexible suture, and an open slot extending from the base of the surgical instrument to the member for securing at least one flexible suture, in which at least one end of said flexible suture is carried. The flexible suture may be a stainless steel wire suture.

The surgical instrument may further include a mechanism for tensioning that comprises a one way clutch that restricts the mechanism from returning to the initial configuration of the mechanism after the surgical instrument is released from a flexible suture encircling a bone.

The surgical instrument may further include a mechanism for applying a plurality of twists that comprises at least two members which are drawn together as tension is applied to a flexible suture and rotate inside a shaft as said plurality of twists are applied. The instrument may also provide an indication of the tension applied to a flexible suture.

The surgical instrument may further include a member for securing at least one end of a flexible suture that is a hole in a rotating shaft. The surgical instrument may restrict a second flexible suture from being tensioned with the same surgical instrument. The surgical instrument may remain in a locked position after tensioning a flexible suture and restrict a second flexible suture from being tensioned with the same surgical instrument.

At lease one embodiment of a surgical instrument may be a single-use instrument for securing parts of a bone using a flexible suture, comprising a mechanism for fixing at least one of said sutures to said instrument prior to said suture encircling said bone, and a second mechanism for tensioning said suture prior to securing said suture by twisting.

Yet another embodiment is a system for securing parts of a bone using flexible sutures comprising a plurality of single-use surgical instruments, each said instrument comprising a mechanism for fixing at least one end of a flexible suture to said instrument prior to said suture encircling said bone.

At least one embodiment of a surgical instrument may be summarized as comprising a member for tensioning a flexible suture encircling a bone, a second member for applying a plurality of twists to the flexible suture, and a base that supports the surgical instrument on the bone during tensioning of the flexible suture. The flexible suture may be a stainless steel wire suture. The surgical instrument may further include a base which comprises an open slot in which the flexible suture is carried. The base preferably rotates less relative to the bone than the number of twists that are applied to the flexible suture. The surgical instrument may comprise a member to cause the flexible suture to break or part at a designated location. The break or part may be set to occur near the end of the plurality of twists that is further away from the bone. The break or part may be set to occur proximate the middle of the plurality of twists.

At least one embodiment of a surgical instrument may be summarized as a surgical instrument comprising a member for tensioning a flexible suture encircling a bone, a second member for applying a plurality of twists to the flexible suture and a third member for decreasing said tension as the plurality of twists are applied. The flexible suture may be a stainless steel wire suture. The surgical instrument may provide an indication of the tension applied to the flexible suture. The member for decreasing tension may decrease the separation between the member for tensioning and the plurality of twists. Also, the member for reducing tension may comprise an elastic member, such as a spring, that is tensioned during tensioning of the flexible suture and released as the plurality of twists are applied. The member for tensioning may comprise one or more elastic members which are deformed as the flexible suture is tensioned.

Another embodiment of a surgical instrument may be summarized as comprising a member for tensioning a flexible suture encircling a bone wherein said mechanism for tensioning comprises at least one member for securing at least one end of said flexible suture, a second member for applying a plurality of twists to said flexible suture, and an open slot extending from base of surgical instrument to said member in which at least one end of said flexible suture is carried. The flexible suture may be a stainless steel wire suture. The member for applying a plurality of twists may comprise an additional member that restricts the member for applying a plurality of twists from returning to its initial configuration after the surgical instrument is released from the flexible suture encircling the bone. The second mechanism for applying a plurality of twists may comprise at least two members which are drawn together and rotate inside a shaft as the plurality of twists are applied. The surgical instrument may provide an indication of the tension applied to the flexible suture. The member for securing at least one end of the flexible suture may be a hole in a rotating shaft. The surgical instrument may remain in a locked position after tensioning the flexible suture and restrict a second flexible suture from being tensioned.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE INVENTION

In the following description, certain specific details are set forth in order to provide a thorough understanding of various embodiments of the invention. However, one skilled in the art will understand that the invention may be practiced without these details. In other instances, well-known structures have not been shown or described in detail to avoid unnecessarily obscuring descriptions of the embodiments of the invention.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings provided herein are for convenience only and do not interpret the scope or meaning of the claimed invention.

References in the document are made to stainless steel wire sutures, which could also refer to any other type of flexible suture.

Figure 1:
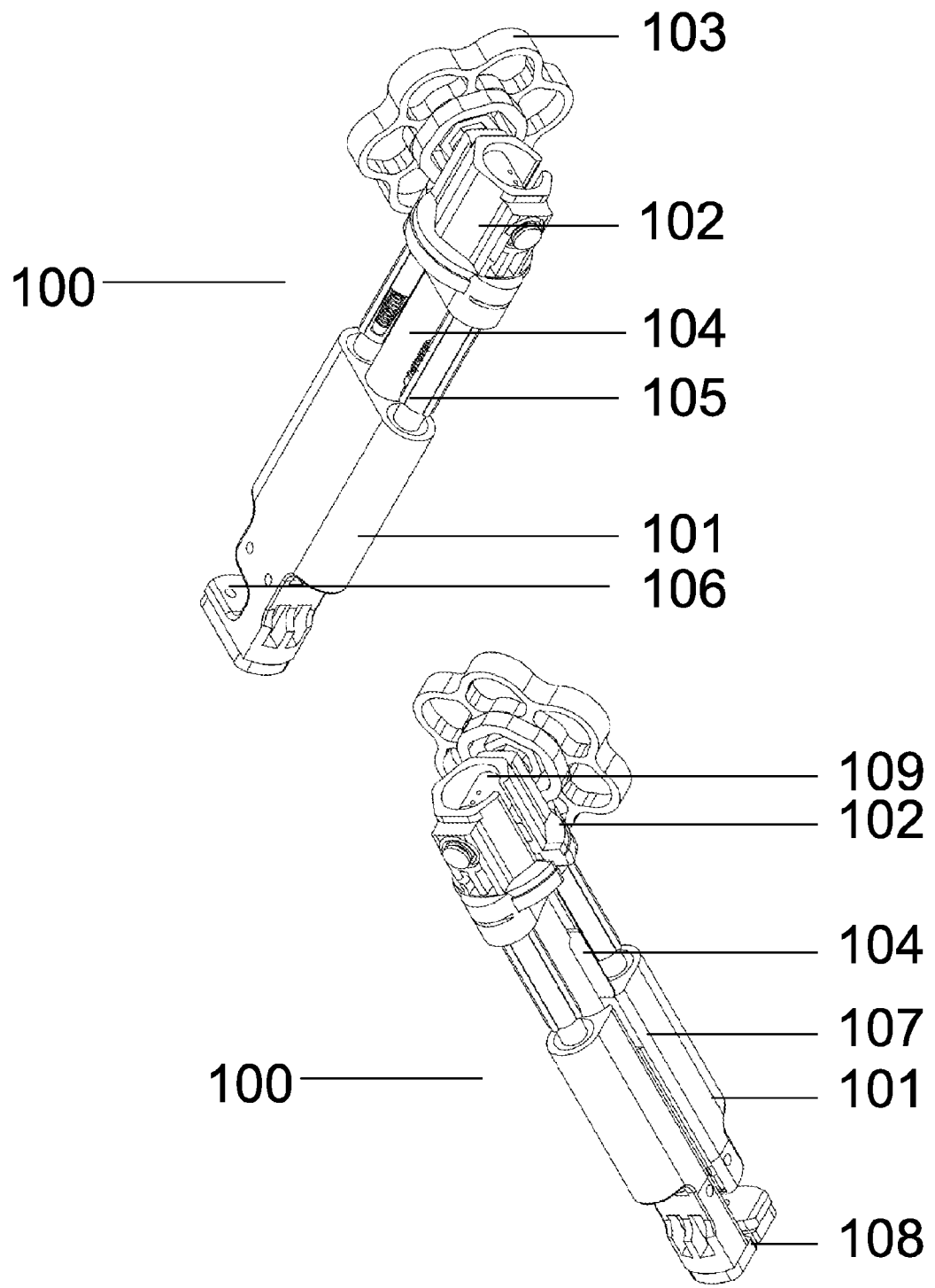
FIG. 1 is a schematic diagram showing two views of a surgical instrument according to one illustrated embodiment.

FIG. 1 shows an assembled view of a surgical instrument according to one illustrated embodiment. Surgical instrument 100 comprises base column 101, rotating head 102, tensioning handle 103, central twisting shaft 104 and pistons 105. Surgical instrument 100 may also have cutting slot 106. Surgical instrument 100 comprises open slot 107 that runs vertically through surgical instrument 100. Surgical instrument 100 is so designed, such that a flexible suture or multiple flexible sutures may be loaded into slot 107 and easily drawn into the center of surgical instrument 100 without being threaded or fed through a lumen or hole. Slot 107 preferably runs through base 108, base column 101, rotating head 102 and central twisting shaft 104. A flexible suture may be secured into tensioning shaft 109 prior to being drawn into open slot 107, or after the flexible suture has been drawn into open slot 107. The surgical instrument may be manufactured in such a way and of such materials that it is to be disposed of after a single use. A single-use instrument may be used to perform a particular action once, or to perform a set of actions, but only on a single patient. An example of performing a particular action once is tensioning and twisting a single flexible suture used to secure a portion of the sternum after a sternotomy. An example of performing a set of actions on a single patient is tensioning and twisting all, or at least more than one of, the flexible sutures used to secure the sternum after a sternotomy. There are several reasons why it may be preferable for a particular surgical instrument to be "single use" including the ability to ensure proper sterilization and the ability to produce a more cost-effective product. Several examples of apparatus that may restrict the number of actions a particular surgical instrument may perform include a mechanism that locks the device in a position after the first use such that it cannot be used again, components fabricated out of a material such as plastic that becomes deformed after one or several uses and causes the device to fail, or parts that cannot be sterilized after use.

Figure 2:
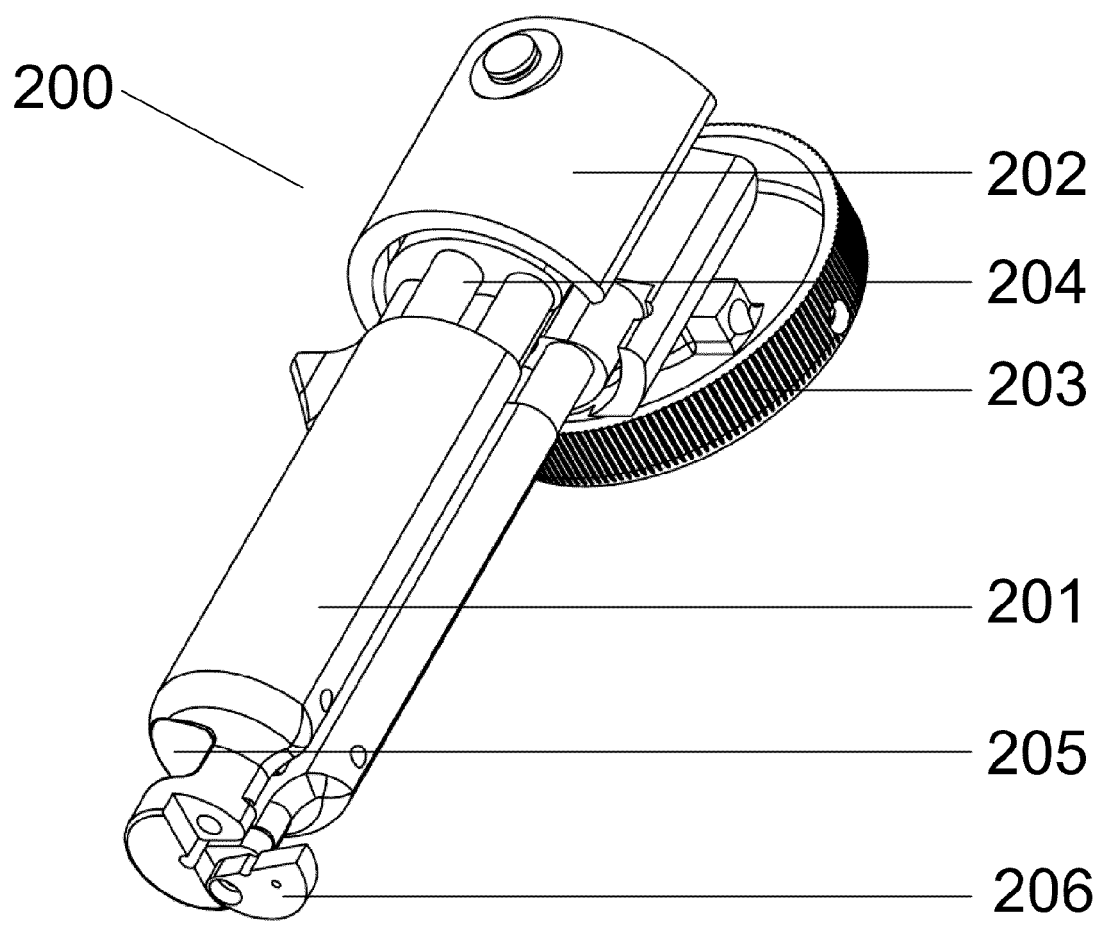
FIG. 2 is a schematic diagram of a surgical instrument according to another illustrated embodiment.

FIG. 2 shows an assembled view of a surgical instrument according to another illustrated embodiment. Surgical instrument 200 comprises base column 201, rotating head 202, and tensioning handle 203. Also shown are pistons 204 and cutting slot 205. Flexible suture capture lock 206 is also shown.

Figure 3:
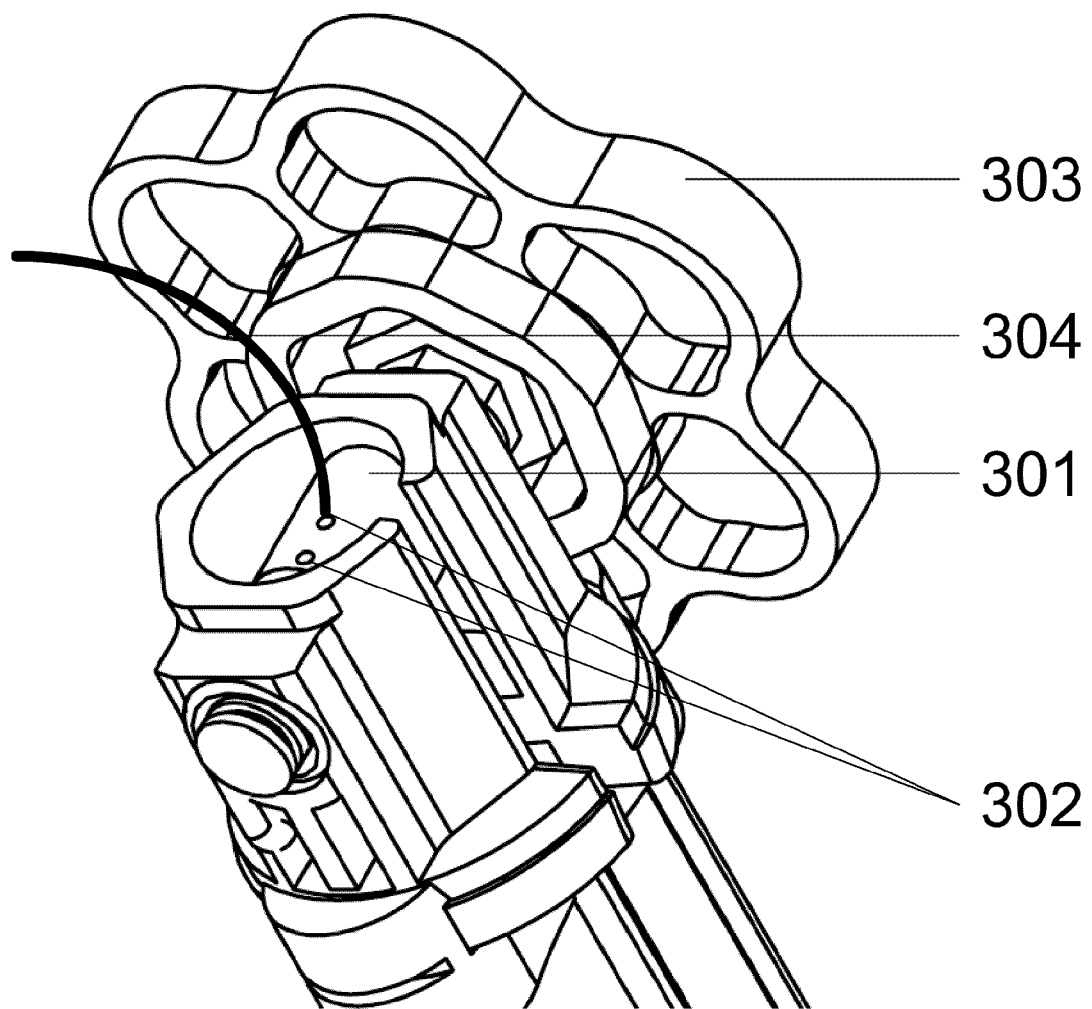
FIG. 3 is a diagram showing a detailed view of a head assembly of a surgical instrument, according to one illustrated embodiment.

FIG. 3 shows one embodiment of how flexible suture 304 may be secured in tensioning shaft 301. One or more small holes 302 may be made in tensioning shaft 301. The ends of flexible suture 304 may be inserted into holes 302. Rotating tensioning shaft 301 by rotating tensioning handle 303 causes flexible suture 304 to wrap around tensioning shaft 301, and so become secured to tensioning shaft 301. In other embodiments there may be multiple holes 302 at various angles that allow flexible suture 304 to be easily inserted, regardless of the orientation of tensioning shaft 301. Flexible suture 304 may be inserted into small holes 302 either horizontally, from below, or from above. Flexible suture 304 may be secured to tensioning shaft 301 prior to flexible suture 304 being brought proximate to or encircling a bone.

Figure 4:
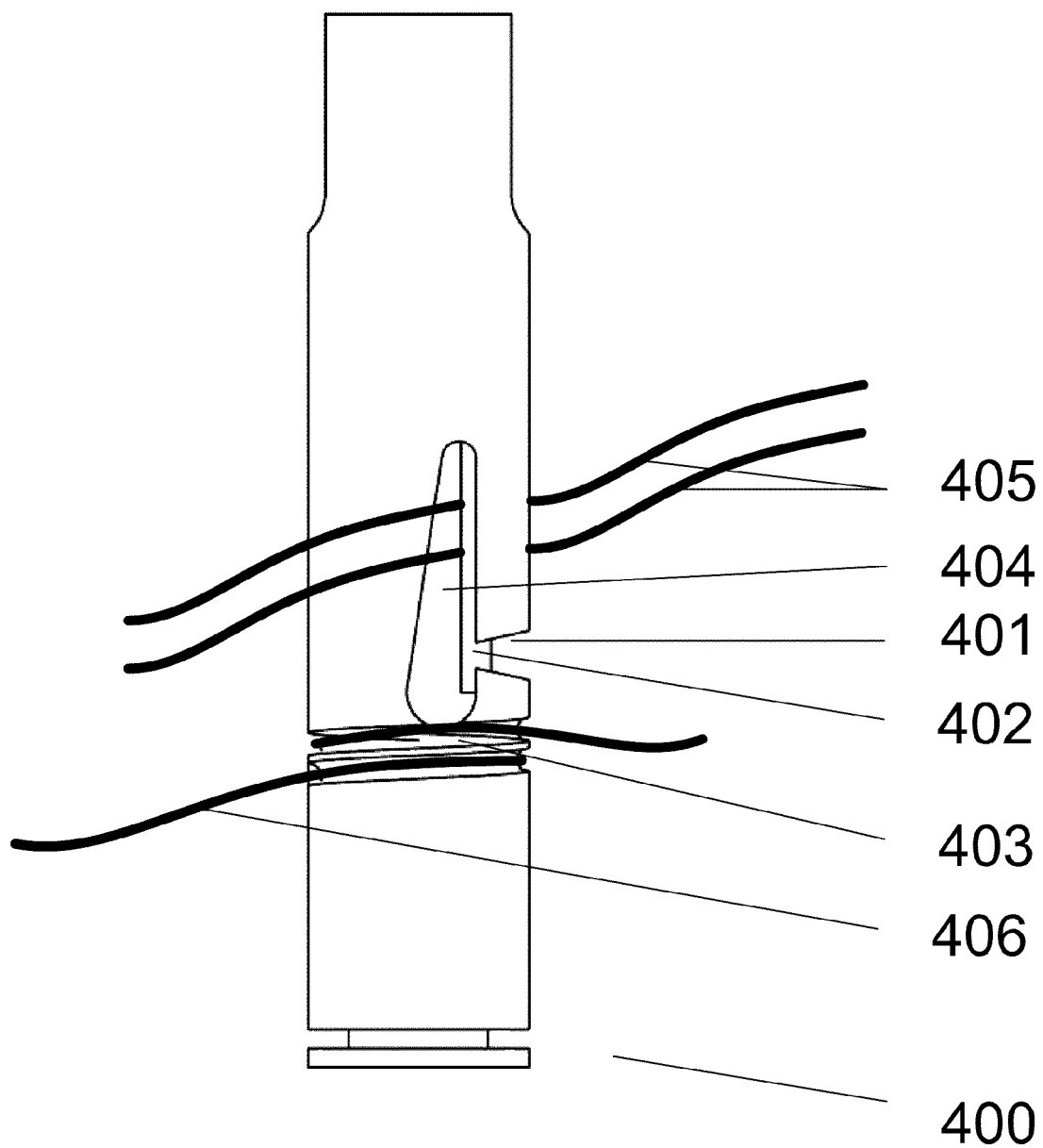
FIG. 4 is a diagram showing a detailed view of a tensioning shaft according to one illustrated embodiment.

FIG. 4 shows an alternate embodiment of a tensioning shaft 400. Opening 401 is large enough that two flexible sutures 405 may easily be pulled into slot 404. One way latch 402 allows flexible sutures 405 to easily enter opening 401 and slot 404, but do not allow flexible sutures 405 to escape from opening 401. Capturing flexible sutures 405 in slot 404 secures flexible sutures 405 to tensioning shaft 400. Another method of securing a flexible suture 406 to tensioning shaft 400 is to use groove 403. Flexible suture 406 may be held in groove 403, and rotated together with tensioning shaft 400. As flexible suture 406 is rotated with shaft 400, it becomes secured to tensioning shaft 400. Flexible sutures 405, 406 may be secured to tensioning shaft 400 prior to flexible sutures 405, 406 being brought proximate to or encircling a bone.

Figure 5:
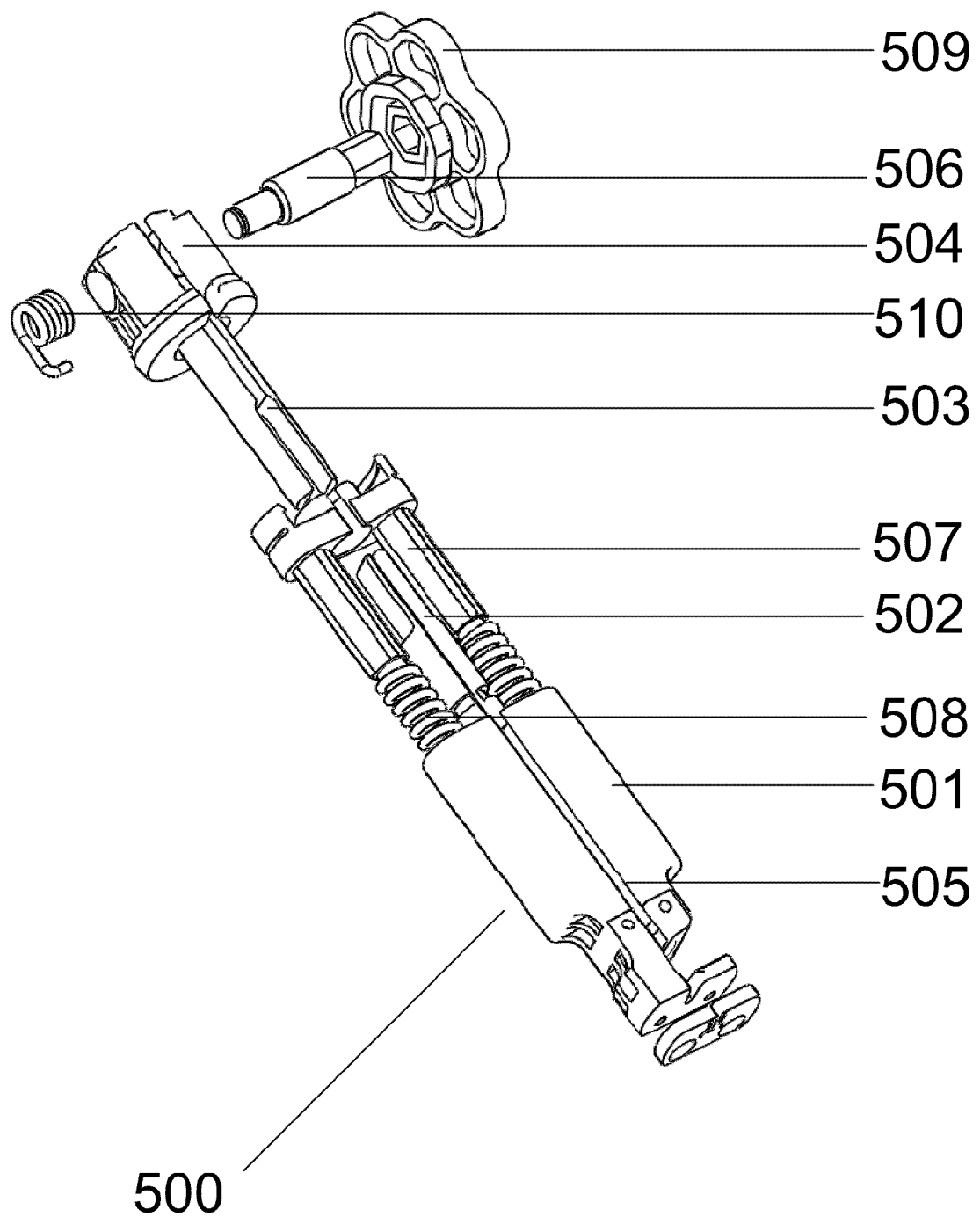
FIG. 5 is a diagram showing an exploded view of a surgical instrument according to one illustrated embodiment.

FIG. 5 shows an exploded view of a surgical instrument 500 according to one illustrated embodiment. Surgical instrument 500 contains base column 501, lower central twisting shaft 502, upper central twisting shaft 503 and twisting head 504. Open slot 505 may be present which runs through the length of surgical instrument 500. Slot 505 allows flexible sutures to be easily loaded into surgical instrument 500 and into tensioning shaft 506. One or more pistons 507 may sit on top of springs 508, which fit into shafts in base column 501. As flexible sutures are twisted around tensioning shaft 506, by rotating tensioning handle 509, tension is applied to the flexible sutures. This tension is maintained by force from springs 508 on pistons 507. As the tension is increased, by further twisting tensioning shaft 506, pistons 507 move downwards into the base column 501 causing springs 508 to compress. The two part design of central twisting shaft 502, 503 enables central twisting shaft 502, 503 to shorten as pistons 507 move downward into base column 501. Lower central twisting shaft 502 is able to move upwards into upper central twisting shaft 503. One way clutch spring 510 fits over tensioning shaft 506 and restricts tensioning shaft 506 to rotate in one direction only. Thus, as tension is applied to the flexible sutures as tensioning shaft 506 is rotated, this tension is maintained, even if tensioning handle 509 is released, as one way clutch spring 510 does not allow tensioning shaft 506 to counter-rotate, which would release the tension. In this way, increasing tension on the flexible sutures may be maintained, until the desired tension is achieved.

Figure 6:
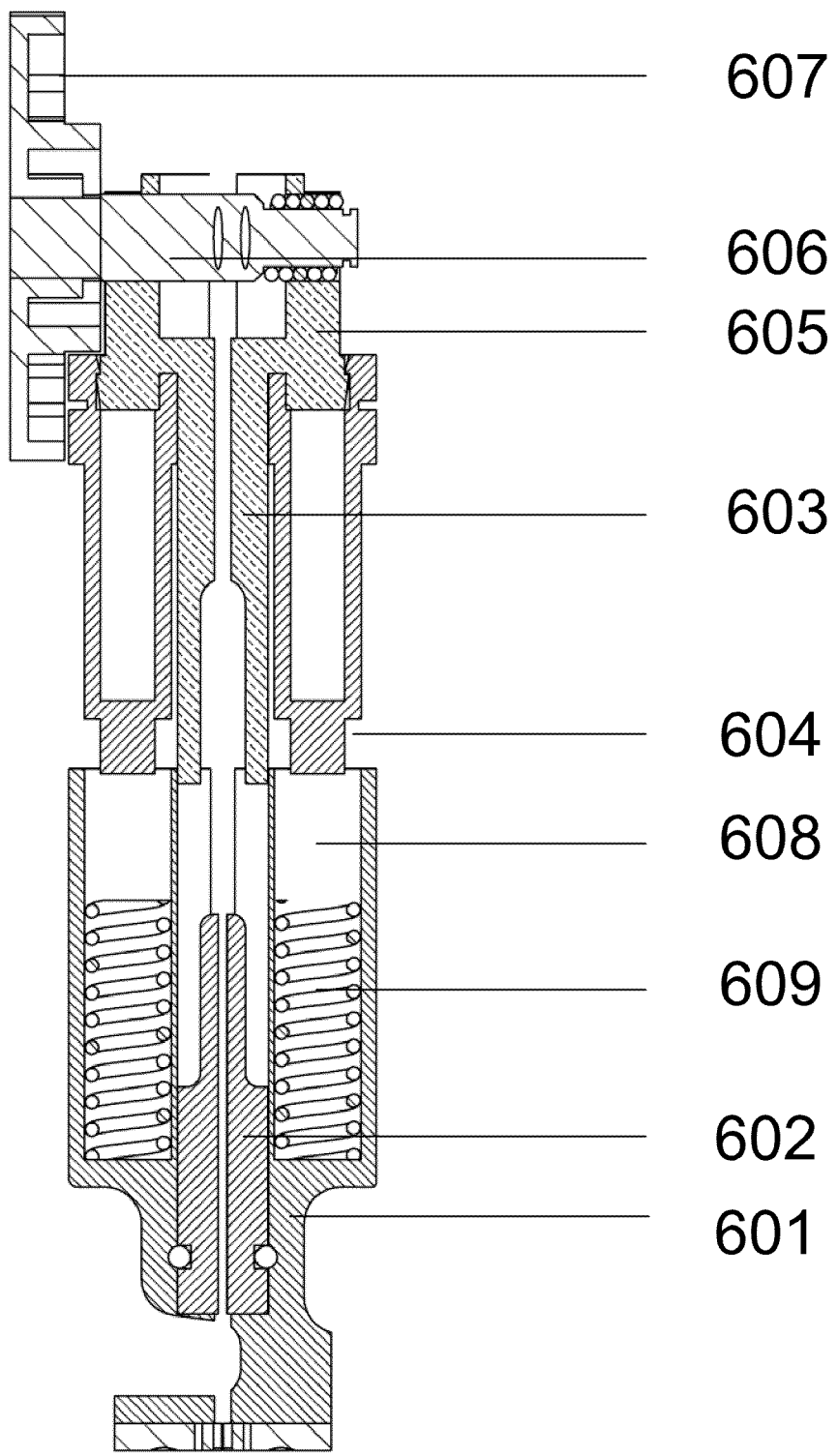
FIG. 6 is a diagram showing a cross sectional view of a surgical instrument according to one illustrated embodiment.

FIG. 6 shows a cross section of one embodiment of a surgical instrument, showing in detail the internal mechanisms. Rotating upper twisting shaft 603 causes lower twisting shaft 602 to rotate. Lower twisting shaft 602 and upper twisting shaft 603 fit together in such a way that they are able to rotate within base column 601, and also may compress together, as pistons 604 move downwards into shafts 608 in base column 601. This mechanism allows twisting head 605, tensioning shaft 606, and tensioning handle 607 also to move downwards. In another embodiment, springs 609 may be replaced by a pneumatic seal at the end of pistons 604. The air trapped in shafts 608 by the pneumatic seal provides resistance to the compression motion of pistons 604 in a similar way to the springs. The surgical instrument may comprise of any number of springs 609, pistons 604, and shafts 608 to provide the desired tension to the flexible suture.

Figure 7:
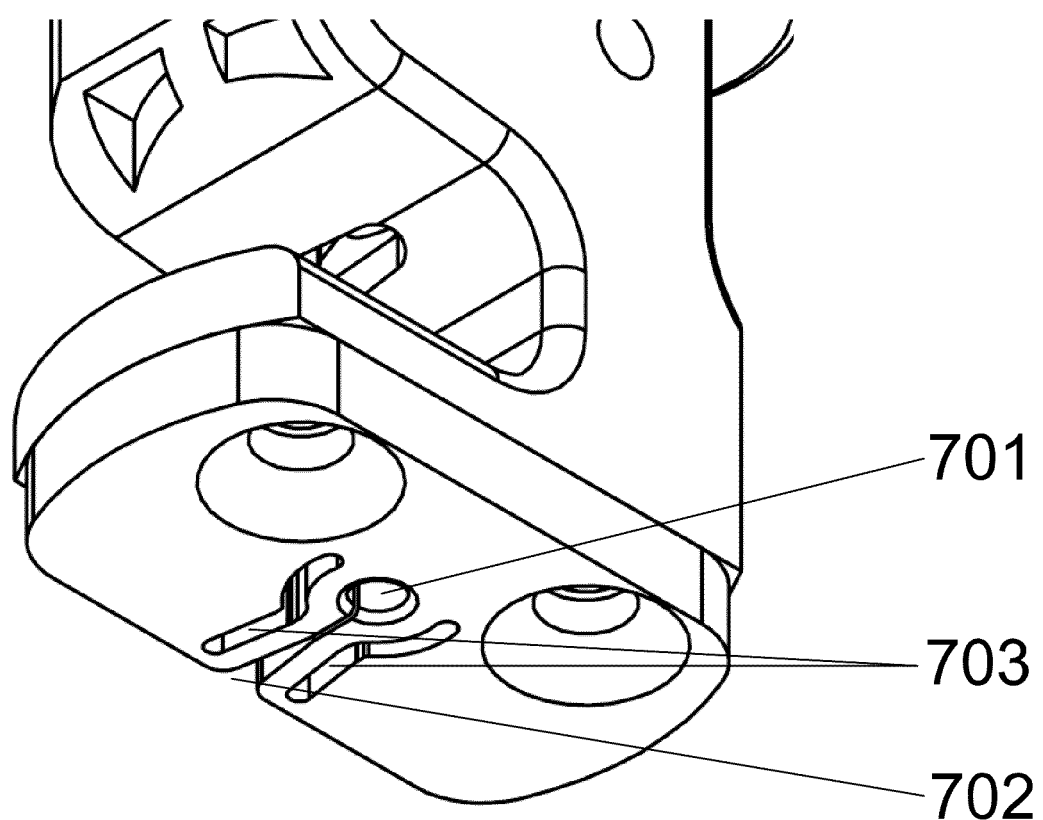
FIG. 7 is a diagram showing a detailed view of a base of a surgical instrument according to one illustrated embodiment.

FIG. 7 shows a base of a surgical instrument in one embodiment, with central opening 701 into which flexible sutures may be drawn through slot 702. The base of the surgical instrument comprises additional flex slots 703, which allow the material surrounding central opening 701 to deform sufficiently to allow the flexible sutures to be drawn easily into central opening 701, where the flexible sutures may be held in place. Once the flexible sutures are drawn into central opening 701, the material between central opening 701 and flex slots 703 returns to its relaxed shape and restrains the sutures in central opening 701.

Figure 8:
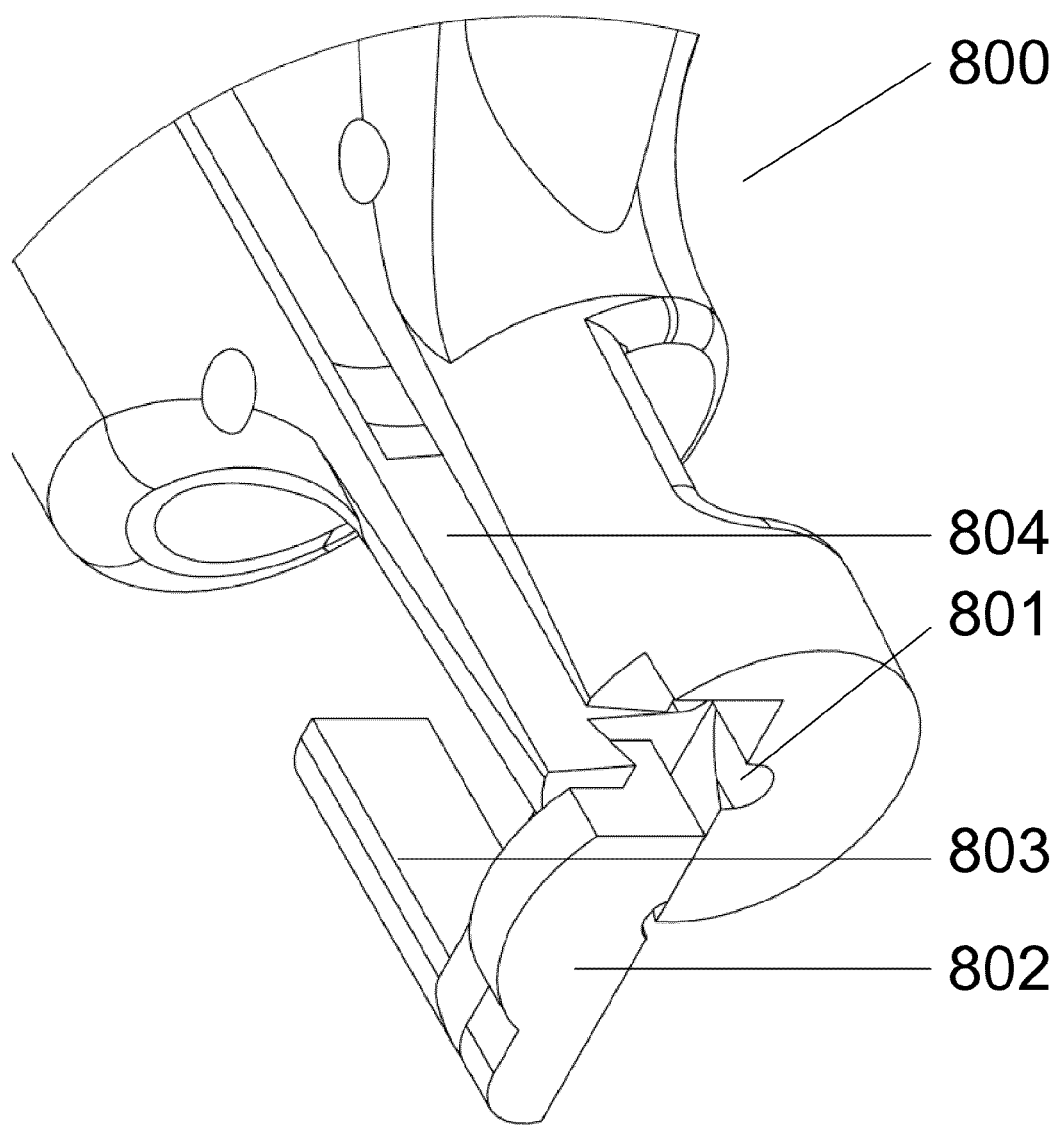
FIG. 8 is a diagram showing a detailed view of a base of a surgical instrument according to another illustrated embodiment.

FIG. 8 shows a base of a surgical instrument 800 in an alternate embodiment, with central opening 801 into which flexible sutures may be drawn. Central opening 801 is initially open, allowing the flexible sutures to easily be drawn into slot 804 which runs vertically through surgical instrument 800. Once the flexible sutures have been drawn into central opening 801, sliding lock 802 may be pushed closed, by pushing on lock handle 803, and so capturing the flexible sutures in central opening 801 in the base of surgical instrument 800.

Figure 9:
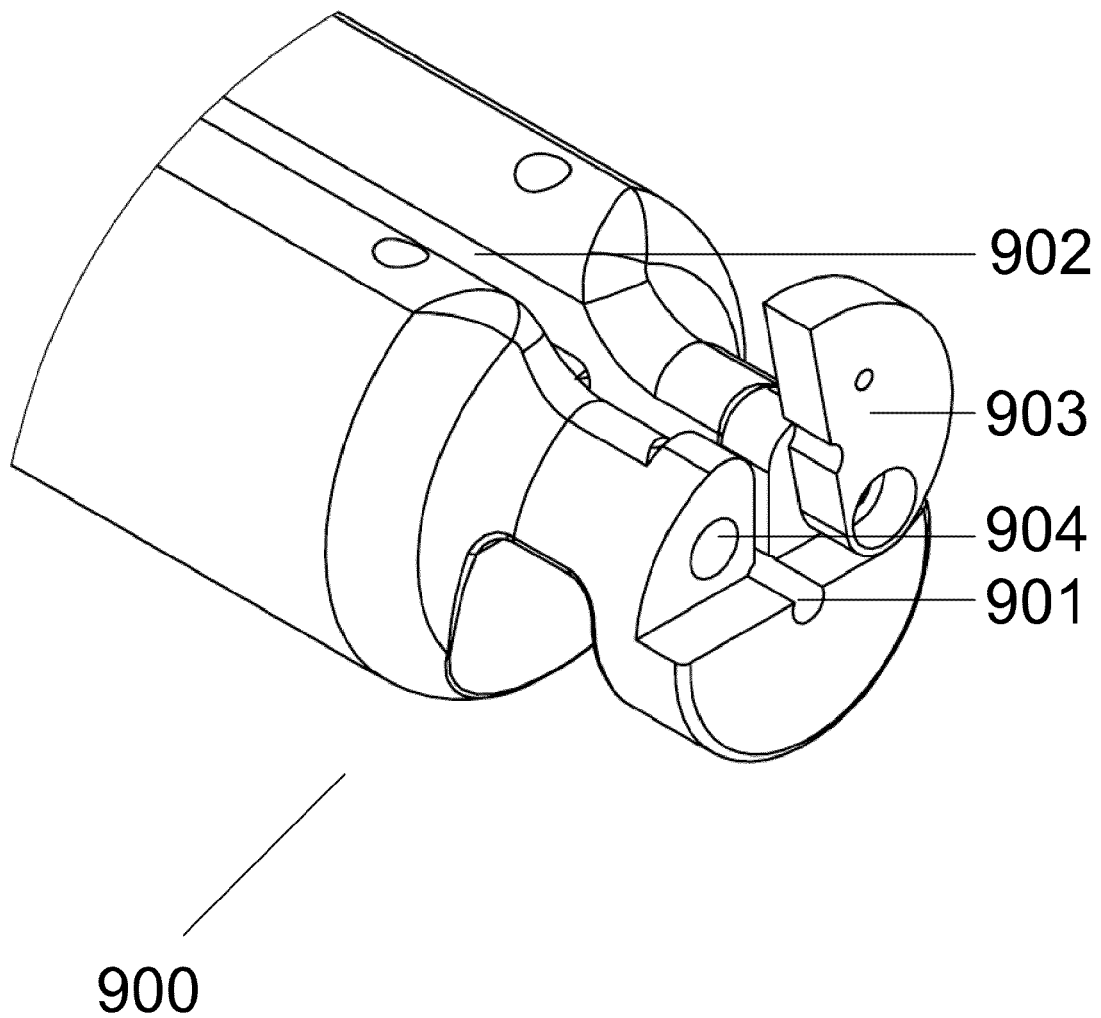
FIG. 9 is a diagram showing a detailed view of a base of a surgical instrument according to another illustrated embodiment.

FIG. 9 shows a base of a surgical instrument in another alternate embodiment, with central opening 901 into which flexible sutures may be drawn. Central opening 901 is initially open, allowing the flexible sutures to easily be drawn into slot 902 which runs vertically through surgical instrument 900. Once the flexible sutures have been drawn into central opening 901, swivel lock 903 may be pushed closed to capture the flexible sutures in central opening 901. Swivel lock 903 may then be held in position by small latch 904 on the base of surgical instrument 900, which locks swivel lock 903 in the closed position.

Figure 10:
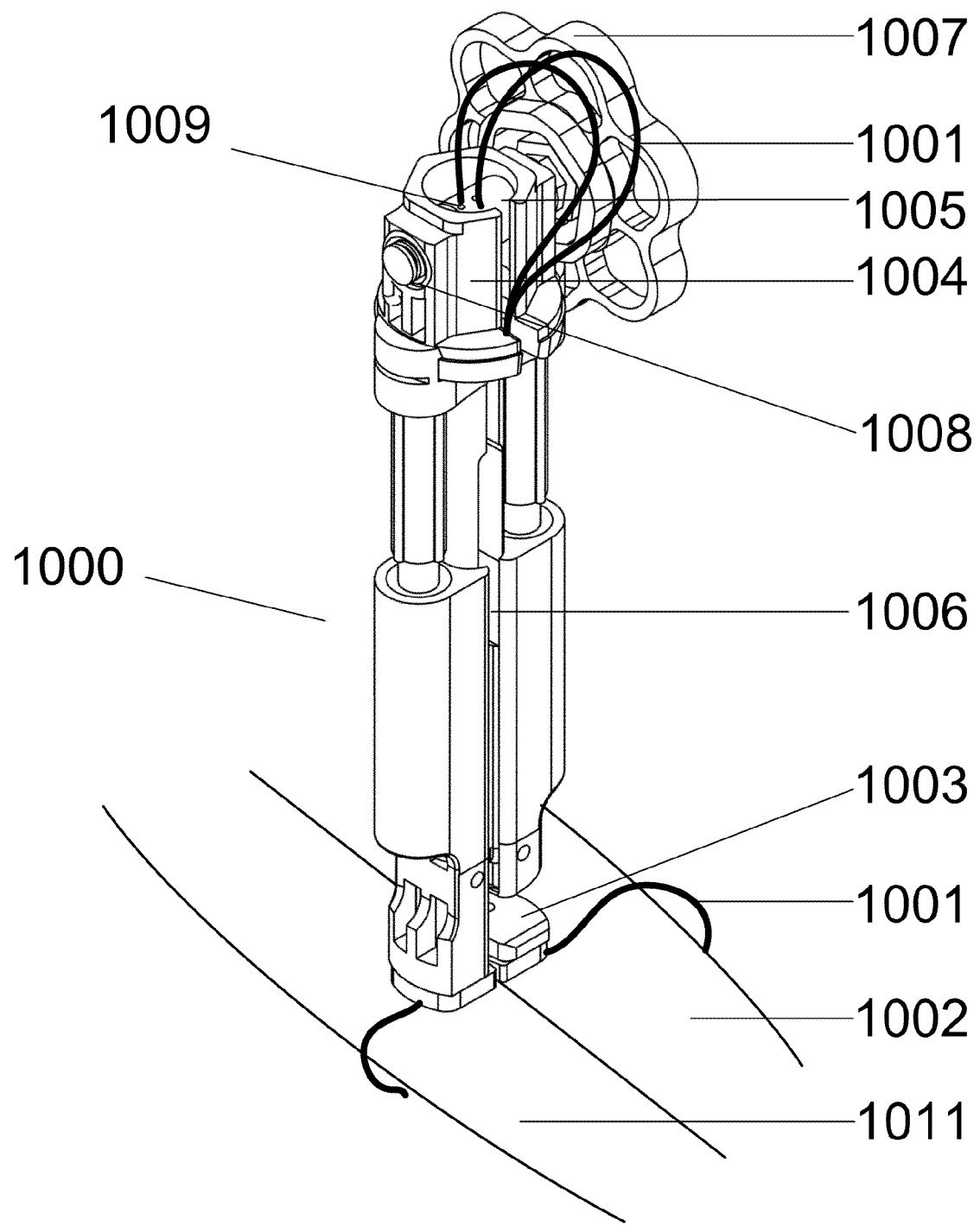
FIG. 10 is a diagram showing a surgical instrument in place on a bone, with flexible sutures, according to one illustrated embodiment.

FIG. 10 is a diagram showing an embodiment of a surgical instrument 1000 being used to tighten flexible sutures around a bone. Flexible suture 1001 is placed around or through parts of bone 1002, 1011 to be secured. The flexible suture 1001 may be drawn through base 1003 of surgical instrument 1000 and upwards through slot opening 1006, towards twisting head 1004 of surgical instrument 1000. Flexible suture 1001 may then be secured in tensioning shaft 1005. Alternatively, flexible suture 1001 may be secured into opening 1009 in tensioning shaft 1005, and then drawn downwards into slot 1006, and then secured in base 1003. Once flexible suture 1001 has been secured in base 1003 and to tensioning shaft 1005, base 1003 may be placed on bone 1002 and tensioning handle 1007 may be rotated to apply tension to flexible suture 1001. Tensioning handle 1007 rotates tensioning shaft 1005, which rotates within one-way clutch mechanism 1008. One-way clutch mechanism 1008 allows tensioning handle 1007 and tensioning shaft 1005 to rotate in only one direction. Rotation of tensioning handle 1007 causes flexible suture 1001 to rotate around tensioning shaft 1005 and applies tension to flexible suture 1001. This tension may be progressively increased by continuing to rotate tensioning handle 1007. Flexible suture 1001 is drawn further up into surgical instrument 1000, through a small opening at the base and tension is applied to the flexible suture 1001 surrounding bone 1002, 1011. As tension is applied, the separated parts of bone 1002, 1011 are drawn together. Tensioning handle 1007 is removable from surgical instrument 1000, which allows multiple surgical instruments to be used together in a restricted space, without tensioning handles 1007 becoming entangled, or impacting the operation of other surgical instruments within close proximity.

Figure 11:
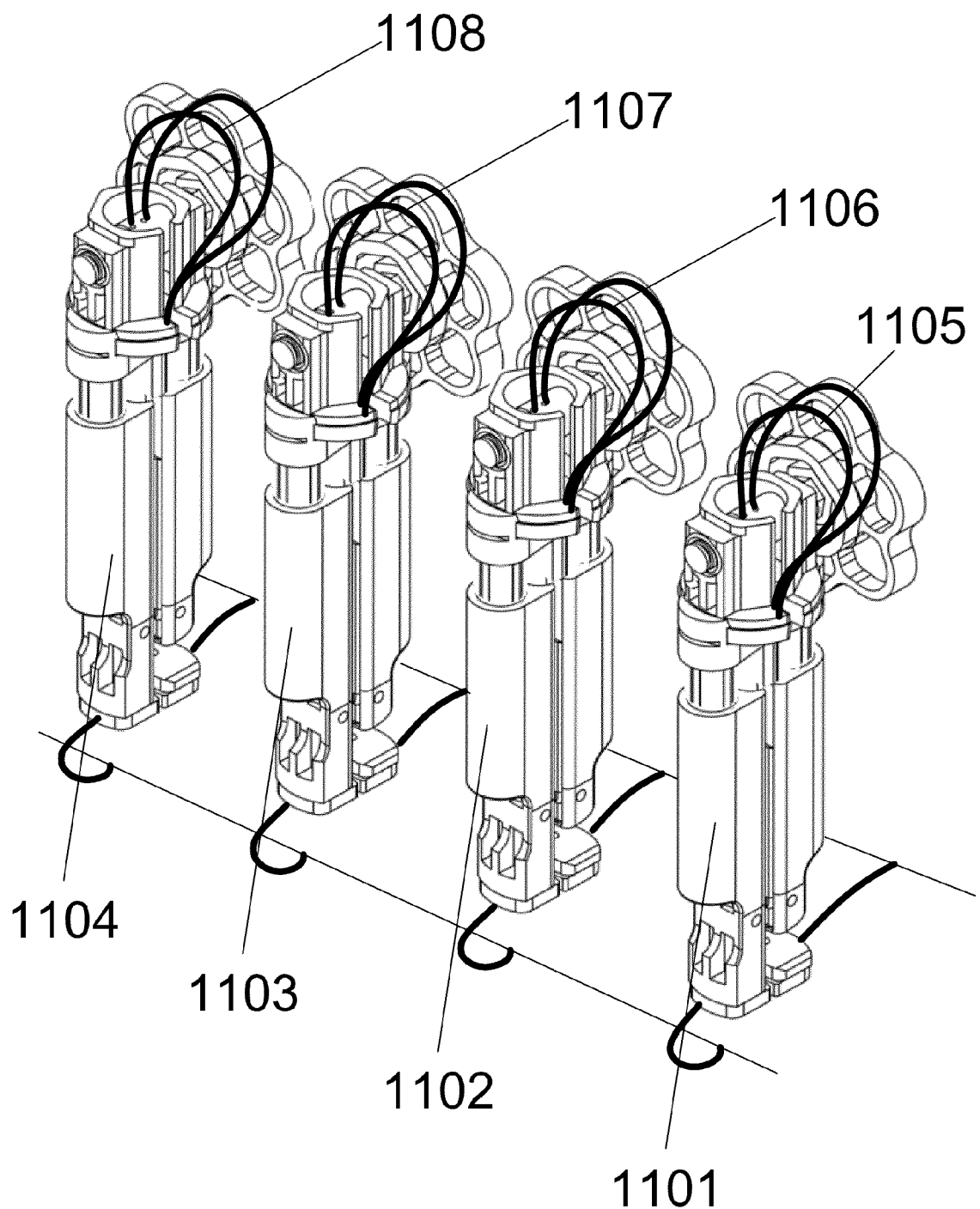
FIG. 11 is a diagram showing multiple surgical instruments in place on a bone, with multiple flexible sutures, according to one illustrated embodiment.

FIG. 11 is a diagram showing an embodiment of multiple surgical instruments being used in parallel to secure a bone. A surgeon may first use surgical instrument 1101 to apply tension to flexible suture 1105. Surgical instrument 1101 may be left in position and second surgical instrument 1102 may now be used to apply tension to second flexible suture 1106. Additional surgical instruments 1103 and 1104 may be added in a similar manner to apply tension to flexible sutures 1107 and 1108. Once two or more surgical instruments have been used to apply tension to two or more different flexible sutures, the surgeon may return to any surgical instrument and increase the tension on the corresponding flexible suture. In this way, multiple surgical instruments may be used in a single procedure to accurately adjust the tension on multiple flexible sutures to the preferred tension. This technique gives the surgeon the ability to precisely adjust each flexible suture to the desired tension required to hold the bone together, and gives the surgeon the ability to increase the tension on any one flexible suture.

Surgical instruments 1101, 1102, 1103, and 1104 may each comprise a mechanism for securing at least one end of flexible sutures 1105, 1106, 1107, 1108 to the surgical instrument prior to the sutures 1105, 1106, 1107, 1108 being brought proximate to or encircling a bone.

Figure 12:
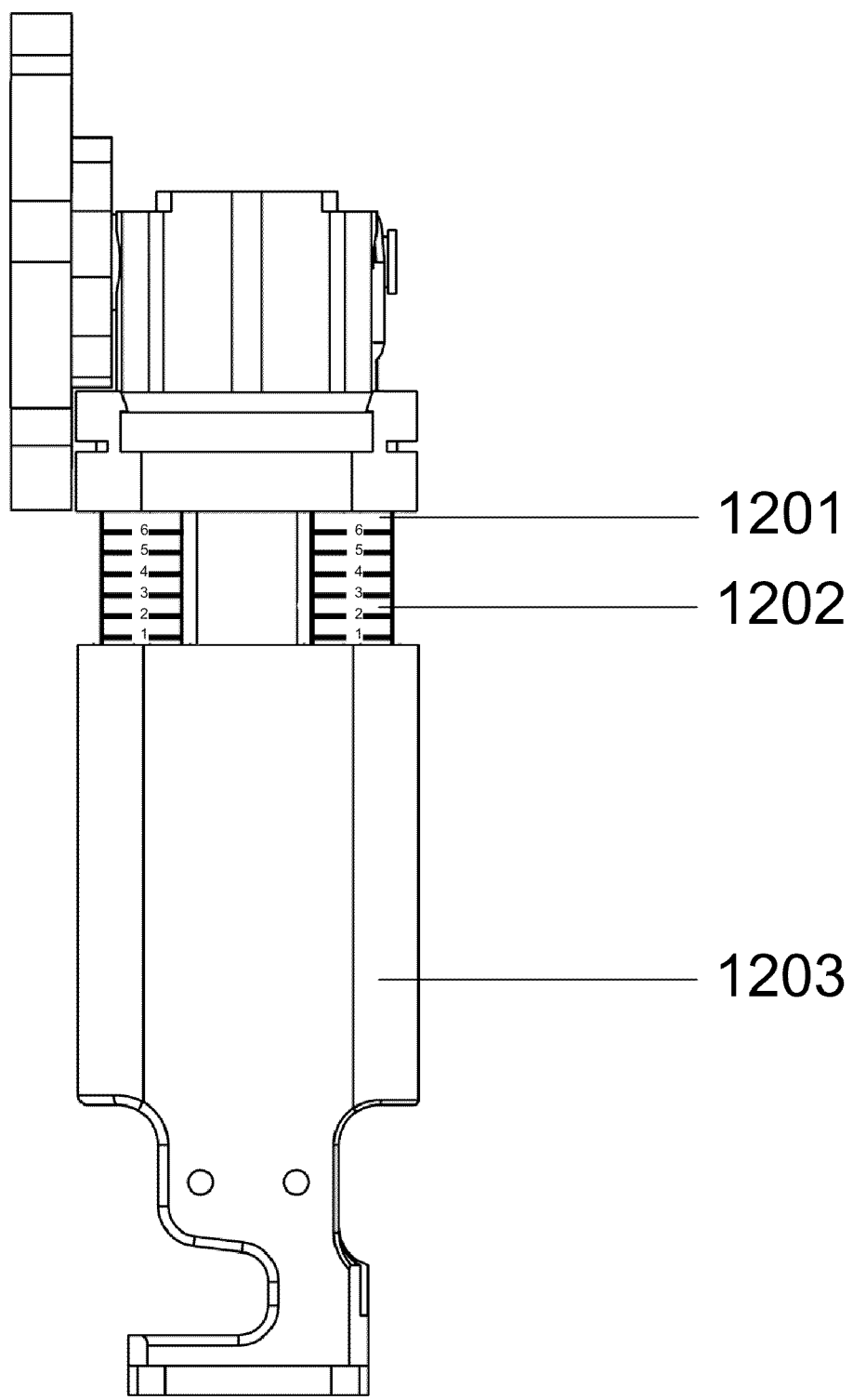
FIG. 12 is a diagram showing a detailed view of a piston assembly with a tension indicator, according to one illustrated embodiment.

FIG. 12 shows a detailed view of one embodiment of a piston assembly and tension indicator. Piston 1201 may include tension indicator 1202, which gives the surgeon an indication of the tension that is being applied to the flexible suture. As more tension is applied to the flexible suture, piston 1201 may move downward into the shaft in base column 1203. This movement may be used to give an indication on piston 1201 of the distance that piston 1201 has moved, and also of the tension that has been applied to the flexible suture.

Once the surgeon is satisfied that all flexible sutures are the desired tension and that the bone is securely held by all the flexible sutures used in the procedure, the surgeon may then begin to secure the flexible sutures in place by twisting each flexible suture together on itself.

Figure 13:
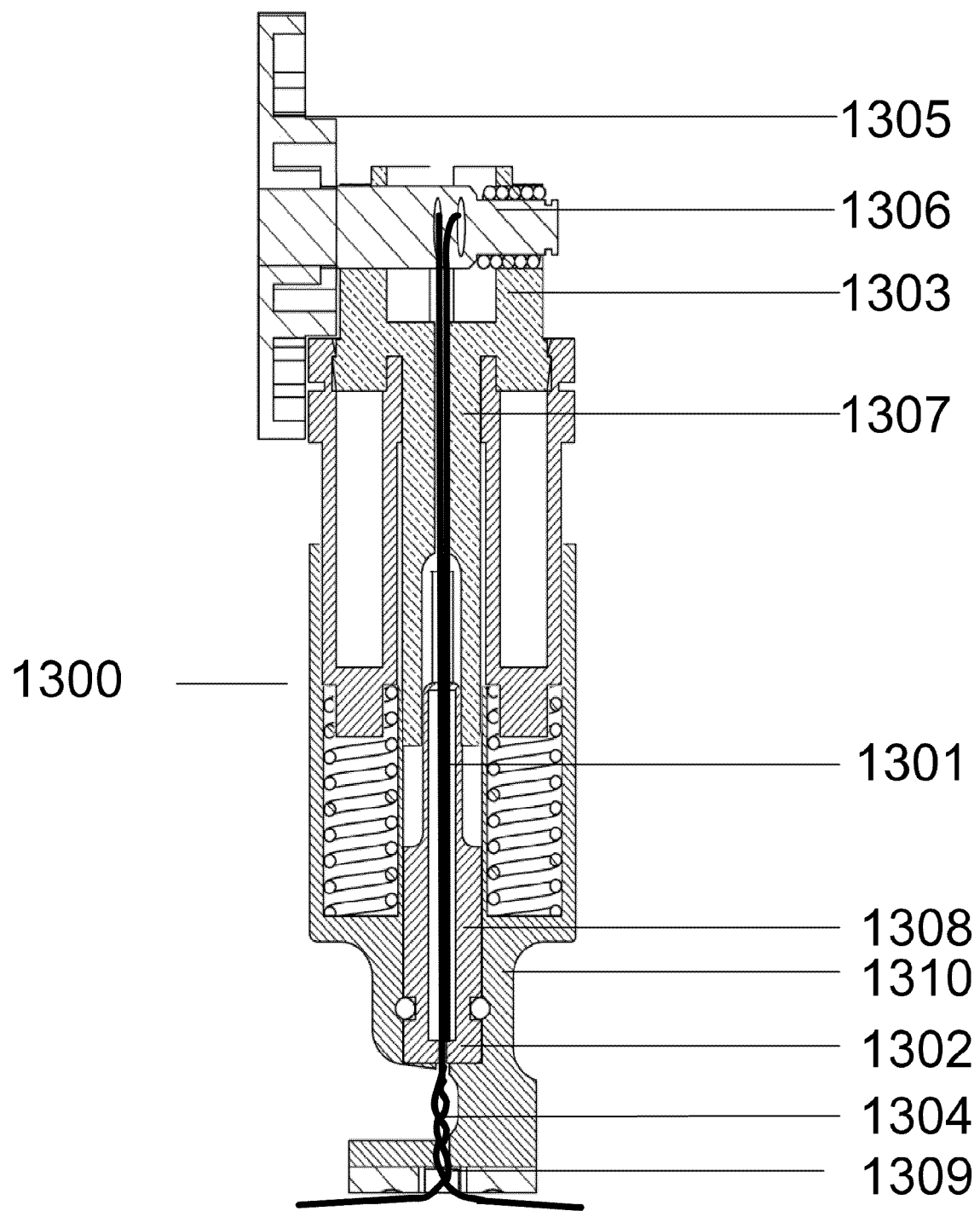
FIG. 13 is a diagram showing a side view of a surgical instrument with flexible sutures, according to one illustrated embodiment.

FIG. 13 shows an embodiment of a surgical instrument 1300 that is able to apply a twist to a flexible suture after the suture has been appropriately tensioned. Twisting head 1303 may be twisted in either a clockwise or anticlockwise direction around the central axis of base column 1310. The entire head assembly including tensioning handle 1305, tensioning shaft 1306 and twisting head 1303 rotate in the direction of rotation applied to twisting head 1303. Base column 1310 does not rotate. This twisting motion of twisting head 1303 is translated into a twisting motion of both upper central twisting shaft 1307 and lower central twisting shaft 1308. Lower central twisting shaft 1308 comprises narrow portion 1302 which restricts the two ends of flexible suture 1301 from twisting about each other within the narrow portion 1302. As lower central twisting shaft 1308 is rotated, the two ends of flexible suture 1301 below narrow portion 1302 begin to twist around each other. This action forms twisted part 1304 of flexible suture 1301 between narrow portion 1302 of lower central twisting shaft 1308 and the narrow opening in the base 1309 of the surgical instrument. After a preferred number of complete rotations of twisting head 1303, flexible suture 1301 may now be sufficiently twisted to provide a secure locking mechanism for flexible suture 1301 that has been applied to the bone. The surgeon may repeat this twisting procedure on each of the surgical instruments that may have been used to secure and tension the flexible sutures on the patient's bone.

Figure 14:
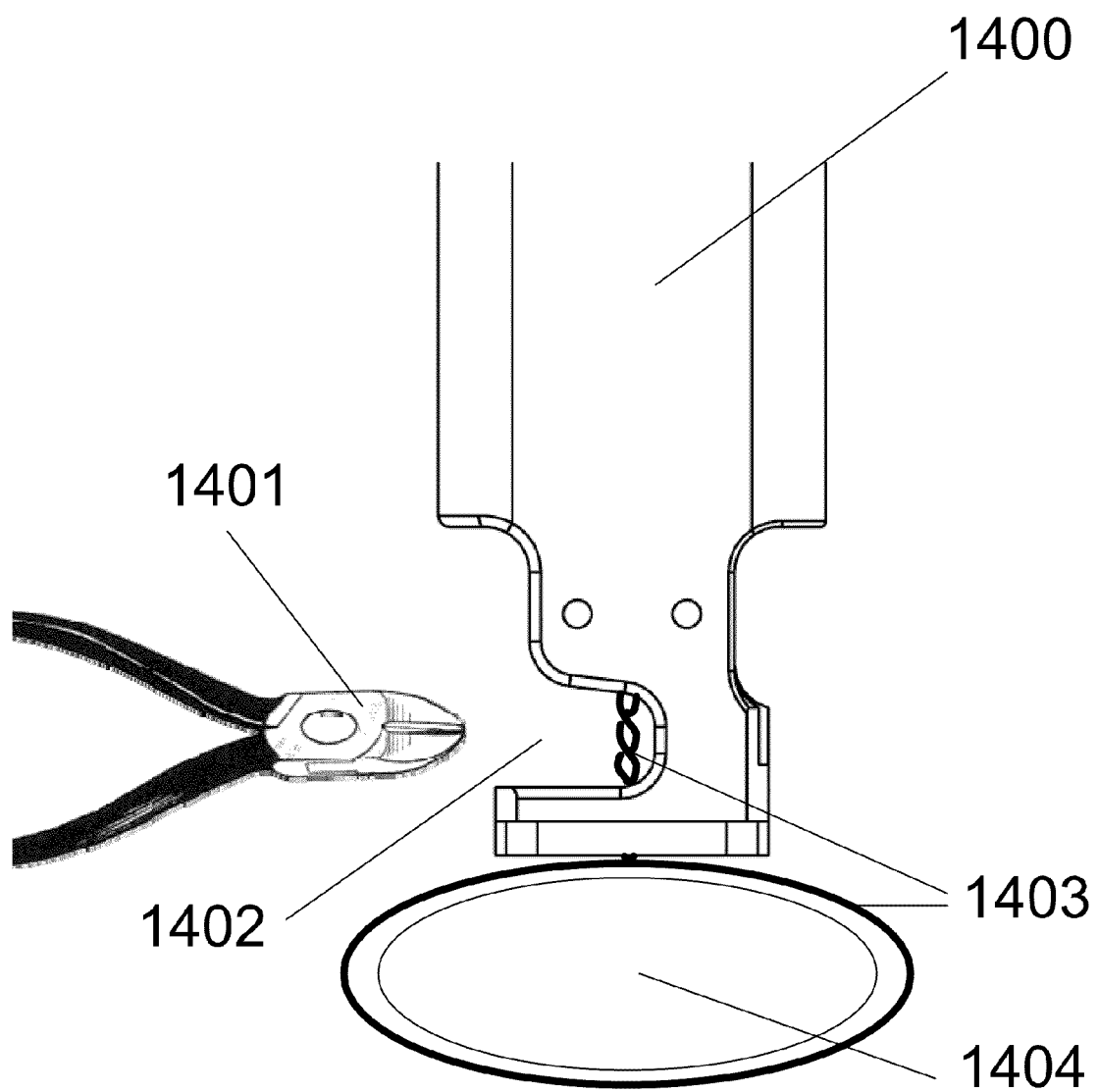
FIG. 14 is a diagram showing cutters being used to cut flexible sutures held within a surgical instrument according to one illustrated embodiment.

FIG. 14 is a diagram showing an embodiment of how a flexible suture may be cut after being tensioned and twisted. Surgical cutters 1401 may be inserted into cutter opening 1402 and cut the twisted flexible suture. Alternatively, surgical instrument 1400 may include a blade for automatically cutting flexible suture 1403. Cutting flexible suture 1403 will release surgical instrument 1400 from flexible suture 1403 attached to bone 1404 and allow surgical instrument 1400 to be removed. In another embodiment of surgical instrument 1400, the narrow part of the lower central twisting shaft (not shown) will be sufficiently narrow or comprise an edge to weaken the flexible sutures that pass through surgical instrument 1400. When a sufficient number of twists have been applied to flexible suture 1403, flexible suture 1403 will automatically break at the top of the twisted section, and release surgical instrument 1400 from the twisted flexible suture 1403.

Figure 15:
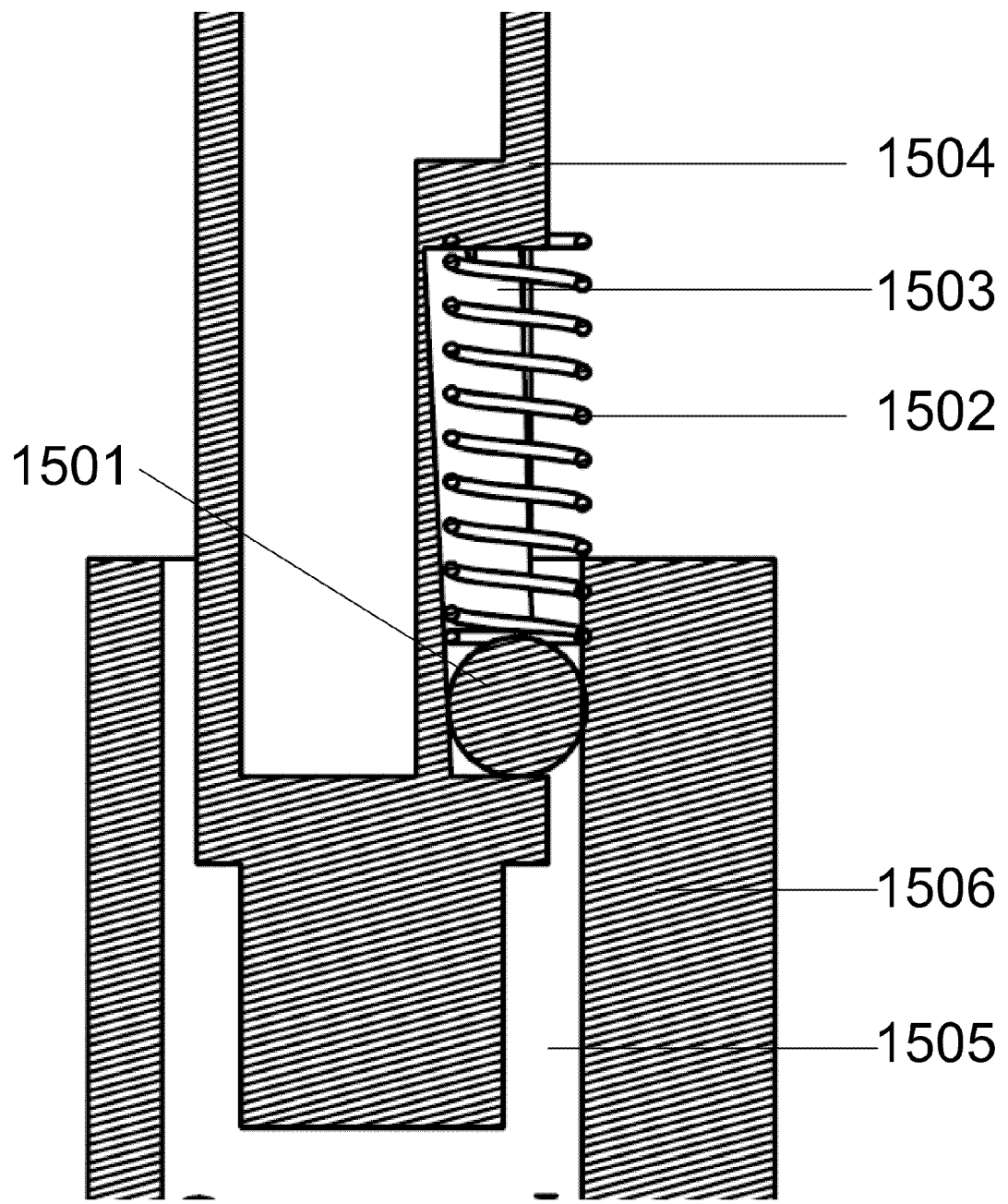
FIG. 15 is a diagram showing a detailed view of a piston assembly, according to one illustrated embodiment.

FIG. 15 shows a detailed view of an embodiment of a one way mechanism on the piston assembly. Piston 1504 may include a mechanism for preventing the head assembly of a surgical instrument from jumping up after cutting a flexible suture loaded into the surgical instrument. Ball 1501 is held in place by spring 1502 in cavity 1503 within piston 1504. When piston 1504 is pushed into shaft 1505 in base column 1506, spring 1502 is compressed, ball 1501 moves into cavity 1503, and piston 1504 is able to move downwards. Piston 1504 is restricted from moving upward and out of shaft 1505 as any upward motion causes ball 1502 to be forced against the wall of shaft 1505 causing sufficient friction such that piston 1504 is unable to move upwards.

Figure 16:
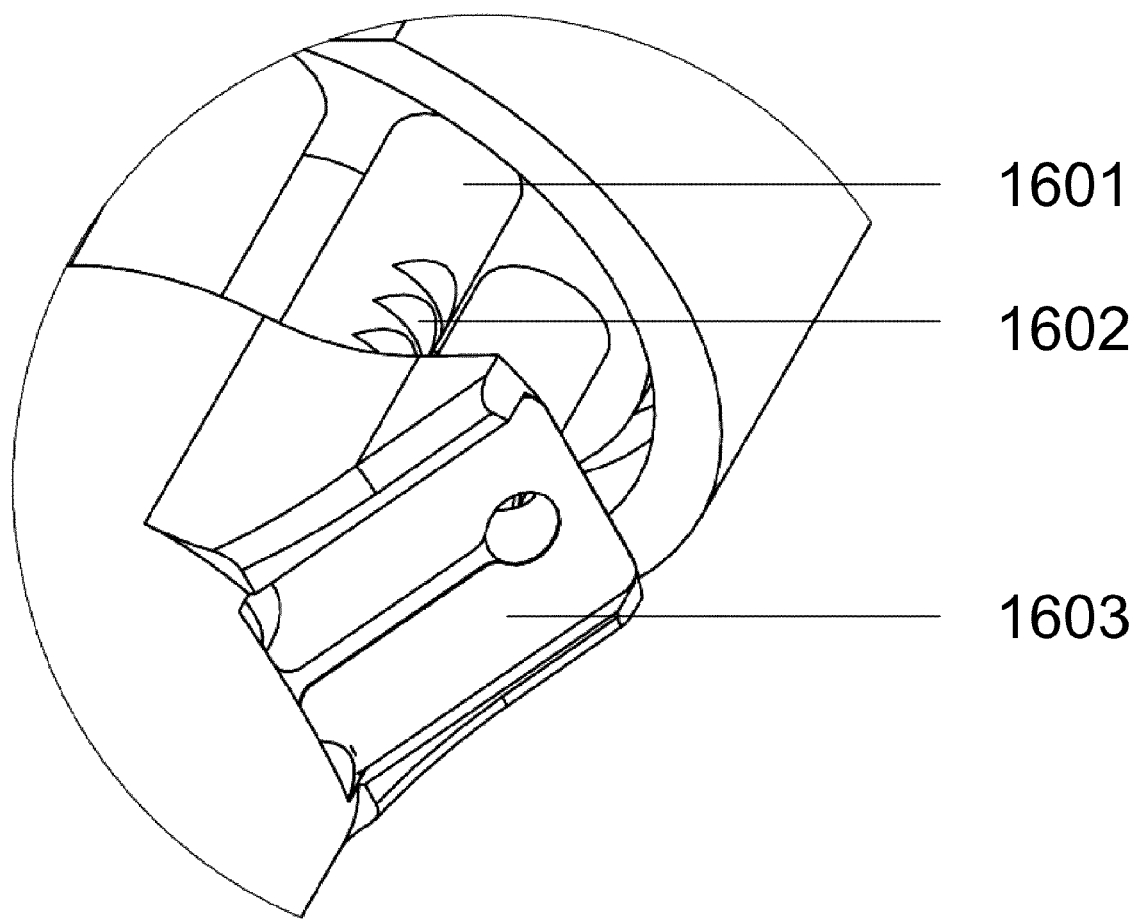
FIG. 16 is a diagram showing a detailed view of a piston assembly, according to another illustrated embodiment.

FIG. 16 shows a detailed view of an embodiment of a one way mechanism on the piston assembly for preventing the head assembly of a surgical instrument from jumping up, after cutting a flexible suture loaded into the surgical instrument. Piston 1601 may have slots 1602 cut into it at regular intervals. Flexible blade 1603 is held with one edge lying at an angle within slots 1602, allowing piston 1601 to move downwards. As piston 1601 moves downwards, blade 1603 may move from one slot 1602 to the one above it. Blade 1603 is able to move easily from one slot to the one above due to the angular orientation of blade 1603 within slot 1602. If piston 1601 attempts to move upwards, the angle of blade 1603 within slot 1602 resists this movement and prevents piston 1601 from moving upwards.

Figure 17:
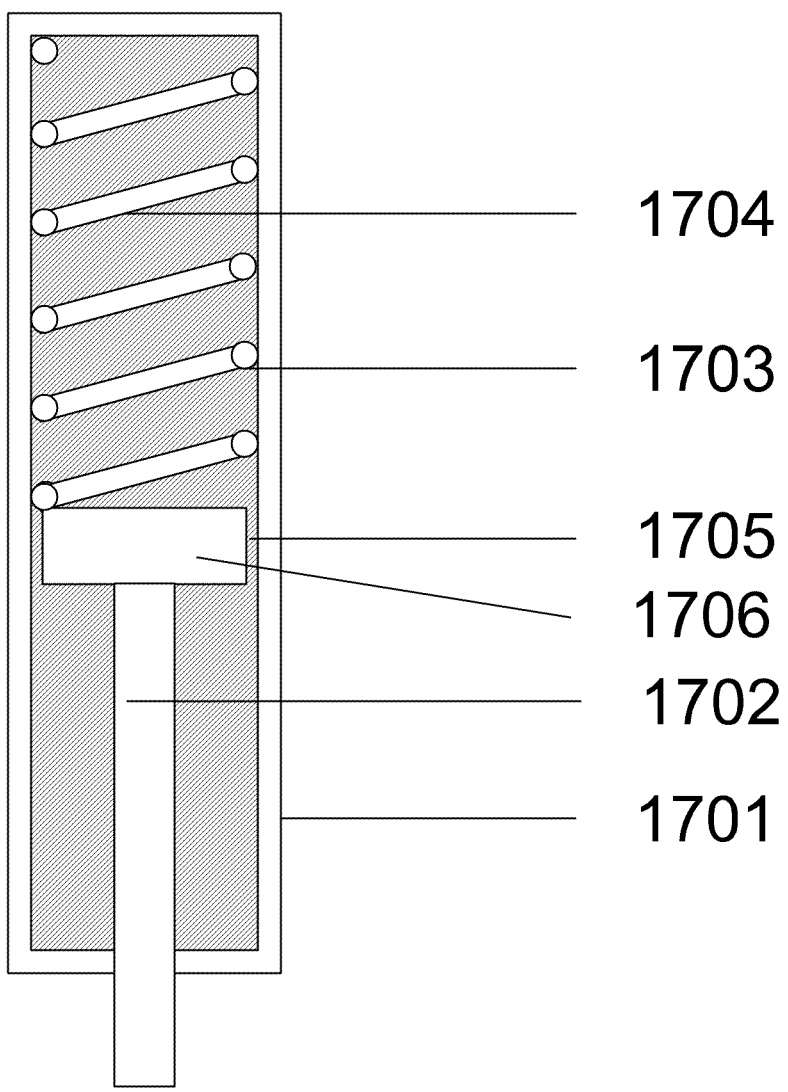
FIG. 17 is a diagram showing a cross sectional view of a piston assembly, according to another illustrated embodiment.

FIG. 17 shows a detailed view of an embodiment of a one way mechanism on the piston assembly for preventing the head assembly of a surgical instrument from jumping up, after cutting a flexible suture loaded into the surgical instrument. In a cross sectional view of shaft 1701 in the base column, spring 1703 inside shaft 1701 in the base column may be enclosed in fluid 1704. Piston 1702 fits into shaft 1701 in the base column, with gap 1705 around piston head 1706. As piston 1702 moves downwards into an opening provided by the base column, spring 1703 slowly compresses, and fluid 1704 is able to move through gap 1705 around piston head 1706. When tension is released by cutting the flexible suture, piston 1702 moves upwards under pressure from spring 1703. This movement is restricted by the flow of fluid 1704 around piston head 1706. This provides a slow upward movement of piston 1702, preventing the head assembly of the surgical instrument mechanism from jumping up.

Figure 18:
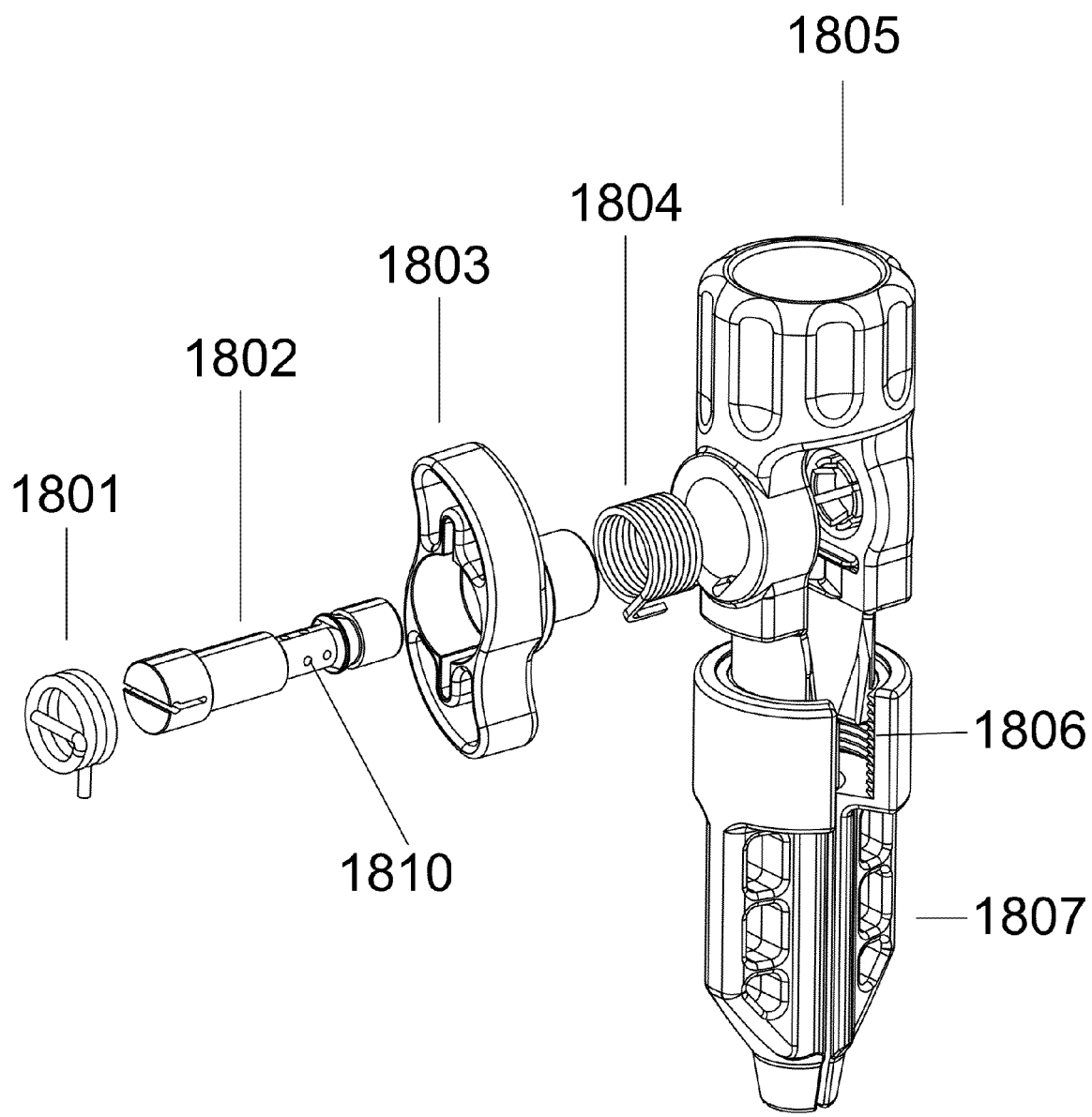
FIG. 18 is a diagram showing an exploded view of a surgical instrument with a mechanism to reduce the upward tension during twisting of flexible sutures according to one illustrated embodiment.

FIG. 18 shows an exploded view of an embodiment of a surgical instrument with a mechanism that enables an initial force to be applied to a flexible suture to tighten the suture around a bone and a second mechanism to decrease the force applied to the flexible suture as a twist is applied to the flexible suture. Applying a sufficiently high initial force enables the flexible suture to be adequately tensioned around a bone such as the sternum. Adjusting or controlling the upward force applied to the ends of a flexible suture as they are being twisted together enables control of the number of twists per length of wire, or twist density, that can be achieved before the flexible suture breaks. Preferably, decreasing the upward force applied to the ends of a flexible suture as they are being twisted together increases the number of twists per length of wire, or twist density, that can be achieved before the flexible suture breaks. Higher twist density is preferable as a higher twist density typically increases the amount of force required to separate the pieces of bone being held together by the flexible suture.

One end of torsion spring 1801 may be fixed to tensioning shaft 1802 and the other end may be fixed to tensioning handle 1803. One way clutch spring 1804 fits over tensioning handle 1803 and preferably restricts tensioning handle 1803 to rotate in one direction only. Turning tensioning handle 1803 causes the end of torsion spring 1801 that is fixed to the tensioning handle to rotate and causes torsion spring 1801 to exert a force on tensioning shaft 1802 in accordance with the angular form of Hooke's law. When sufficient force is applied to tensioning shaft 1802, tensioning shaft 1802 will rotate and wind up the flexible sutures that have been inserted into holes 1810. The force that is applied to the flexible sutures by the rotation of tensioning shaft 1802 is proportional to the force that torsion spring 1801 exerts on tensioning shaft 1802, if frictional forces are ignored.

Twisting head 1805 is rotated to cause two ends of a suture to be twisted around each other. Twisting head 1805 is preferably connected to base column 1807 by threaded section 1806. As twisting head 1805 is rotated it moves downward into base column 1807 and the force applied to the flexible sutures wrapped around tensioning shaft 1802 is decreased. As the force applied to the flexible sutures is decreased, torsion spring 1801 causes tensioning shaft 1802 to rotate and wind up the flexible suture preferably causing a reduced, but non-zero force, to continue to be applied to the flexible sutures during twisting. The mechanical action provided by torsion spring 1801 enables the force applied to flexible sutures wrapped around tensioning shaft 1802 to be gradually reduced as twisting head 1805 is rotated relative to base column 1807. As torsion spring 1801 unwinds to its rest position, the upward force on flexible sutures may be reduced to zero.

Figure 19:
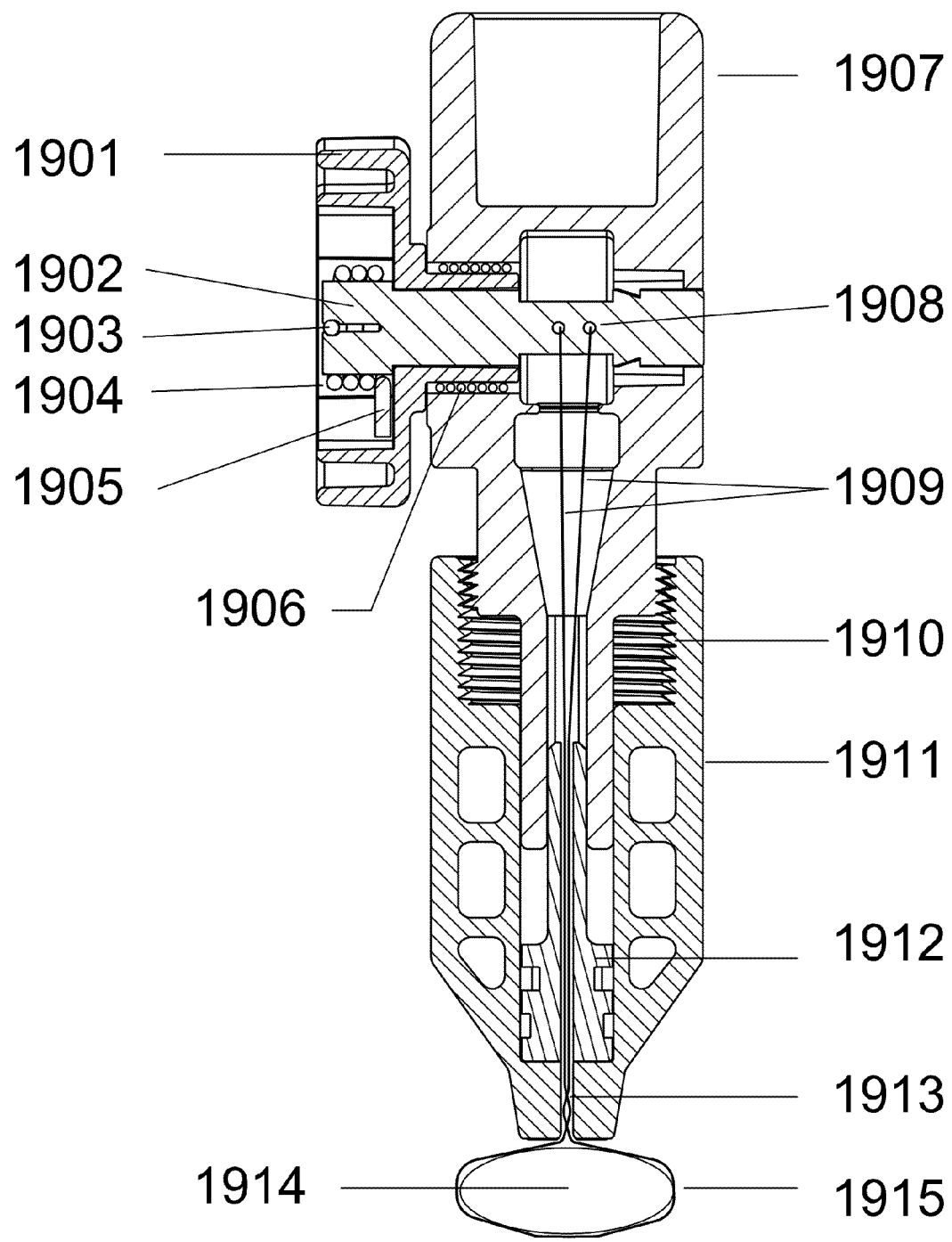
FIG. 19 is a diagram showing a cross section view of a surgical instrument with a mechanism to reduce the upward tension during twisting of flexible sutures according to one illustrated embodiment.

FIG. 19 shows a cross sectional view of the embodiment of the surgical instrument given in FIG. 18. One end 1903 of torsion spring 1904 is fixed to tensioning shaft 1902 and the other end 1905 is fixed to tensioning handle 1901. One way clutch spring 1906 fits over tensioning handle 1901 and preferably restricts tensioning handle 1901 to rotate in one direction only. Turning tensioning handle 1901 causes end 1905 of torsion spring 1904 that is fixed to tensioning handle 1901 to rotate and causes torsion spring 1904 to exert a force on tensioning shaft 1902 in accordance with the angular form of Hooke's law. When sufficient force is applied to tensioning shaft 1902, tensioning shaft 1902 will rotate and wind up ends of flexible sutures 1909 that have been inserted into holes 1908. The force that is applied to the flexible sutures 1909 by the rotation of tensioning shaft 1902 is proportional to the force that torsion spring 1904 exerts on tensioning shaft 1902, if frictional forces are ignored.

Twisting head 1907 is rotated to cause two ends of flexible suture 1909 to form twist 1913 near bone 1914. The two ends of flexible suture 1909 are retained in a slot provided in a central twisting shaft 1912. In this embodiment, the slot in twisting shaft 1912 is sized to retain the two ends of flexible suture 1909. In this embodiment, the slot in twisting shaft 1912 is sized to stop twist 1913 from forming within the slot. Twisting head 1907 is preferably attached to base column 1911 by threaded section 1910. As twisting head 1907 is rotated it moves downward into base column 1911, decreasing the distance between tensioning shaft 1902 and the twisted section 1913 of flexible suture 1909. As the distance decreases, torsion spring 1904 preferably causes tensioning shaft 1902 to rotate and wind the ends of flexible suture 1909 around tensioning shaft 1902. Such winding of flexible suture 1909 during rotation of twisting head 1907 decreases the force applied by torsion spring 1904 to tensioning shaft 1902. The decreasing force applied by torsion spring 1904 enables the upward force applied to ends of flexible suture 1909 wrapped around tensioning shaft 1902 to be gradually reduced as twisting head 1907 is rotated relative to base column 1911. Gradually reducing the force applied to ends of flexible suture 1909 enables sufficient tension to remain in the section of the flexible wire 1915 that surrounds the bone 1914 while maximizing the twist density of the twisted section 1913. As torsion spring 1904 unwinds to its rest position, the upward force on ends of flexible sutures 1909 may be reduced to zero. Testing has shown that applying an initial upward force to ends of flexible sutures 1908 of 220 to 450 newtons, and then reducing the upward tension to less then 20 newtons during 6 to 8 revolutions of twisting head 1907 enables a high twist density to form in a twisted section 1913 of length 8 to 12 mm before the suture breaks near the end of the twisted section 1913 that is further away from the bone from the twisting.

Other embodiments of the surgical instrument could use one of many methods of controlling the force to be applied to the ends of the flexible suture that are to be tightened and twisted. For example, an air piston, springs, or lever system could be used. The force applied to the flexible suture may be increased or decreased as the wire is twisted, depending on the desired twist density. The increase or decrease of force may be applied linearly, exponentially, or in any other relationship with respect to the number of twists applied.

Figure 20:
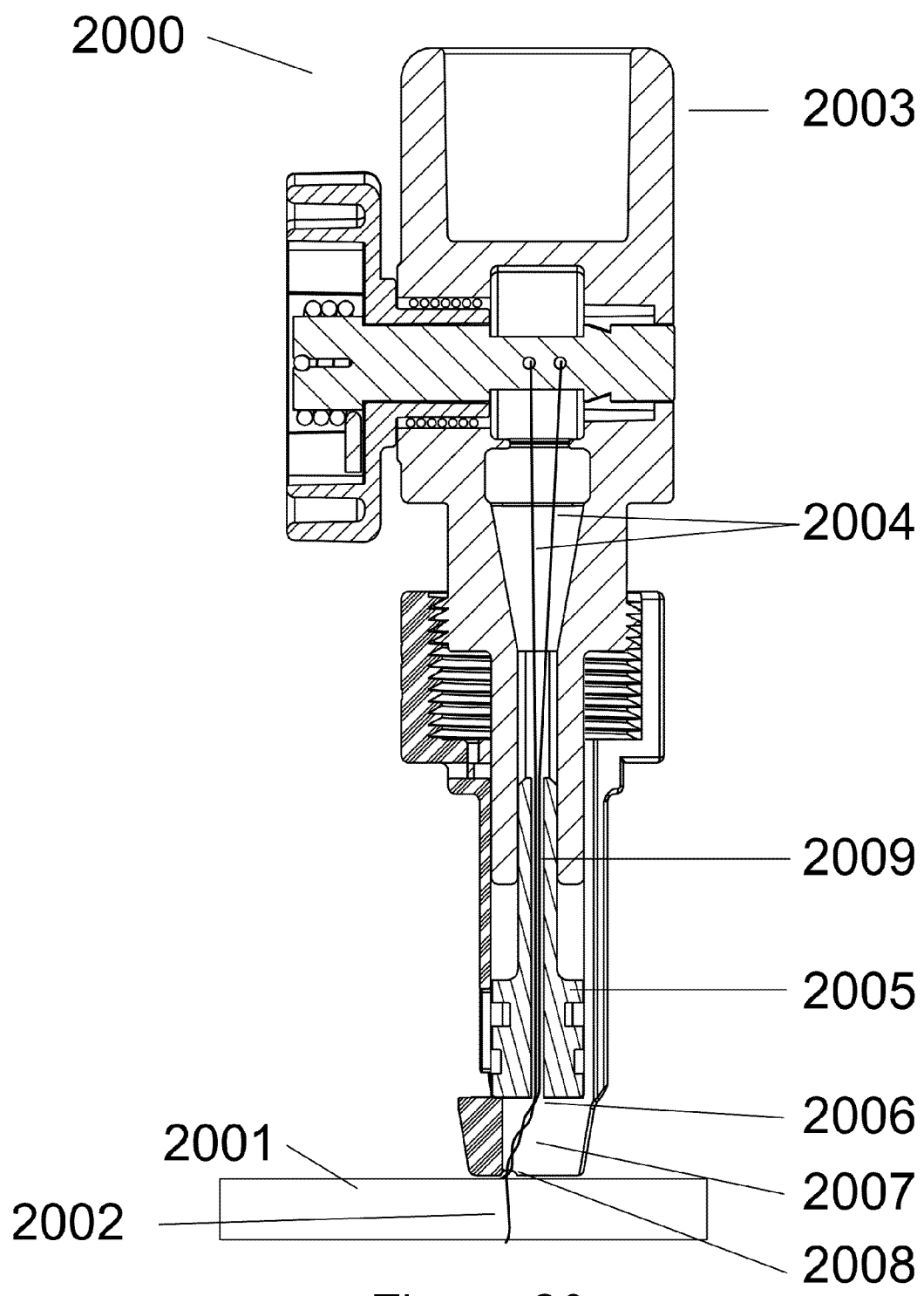
FIG. 20 is a diagram showing a cross section view of a surgical instrument with a bending mechanism to cause wires to break at a particular location according to one illustrated embodiment.

FIG. 20 shows a cross sectional view of an embodiment of a surgical instrument 2000 comprising a mechanism for breaking a wire at a preferred location. The ends of flexible suture 2004 are wrapped around bone 2001 and placed inside a narrow slot 2009 in central twisting shaft 2005. The length 2002 of flexible suture that is wrapped around bone 2001 is held in groove 2008. Groove 2008 is offset from the rotational axis of central twisting shaft 2005.

Rotating twisting head 2003 causes central twisting shaft 2005 to rotate. Central twisting shaft 2005 grips two lengths of flexible suture 2004 and causes the lengths of flexible suture 2004 to rotate about each other and form twisted section 2007. Twisted section 2007 forms at an angle to the portion of flexible suture 2004 that is routed within central twisting shaft 2005 because of the position of groove 2008. As central twisting shaft 2005 rotates, the flexible sutures are repeatedly bent in the region between the base of the central twisting shaft 2005 and the top of twisted portion 2007. The repeated bending causes the sutures to work harden, fatigue, weaken and finally break at preferred breaking location 2006. Increasing the distance that groove 2008 is offset from the rotational access of central twisting shaft 2005 increases the amount of bending the flexible sutures are subjected to at the base of central twisting shaft 2005 and typically reduces the number of rotations of twisting head 2003 required to cause the sutures to part or break at the top of the twisted portion 2007. The preferred location of where the wire will break can be adjusted by controlling the position where the wire is repeatedly bent during rotation. For example, in addition to the previous embodiment, another embodiment of a medical device could preferably part the wire in the middle of a twisted section of wire, and yet another embodiment could part the wire a specified distance above the twisted section of wire.

Figure 21:
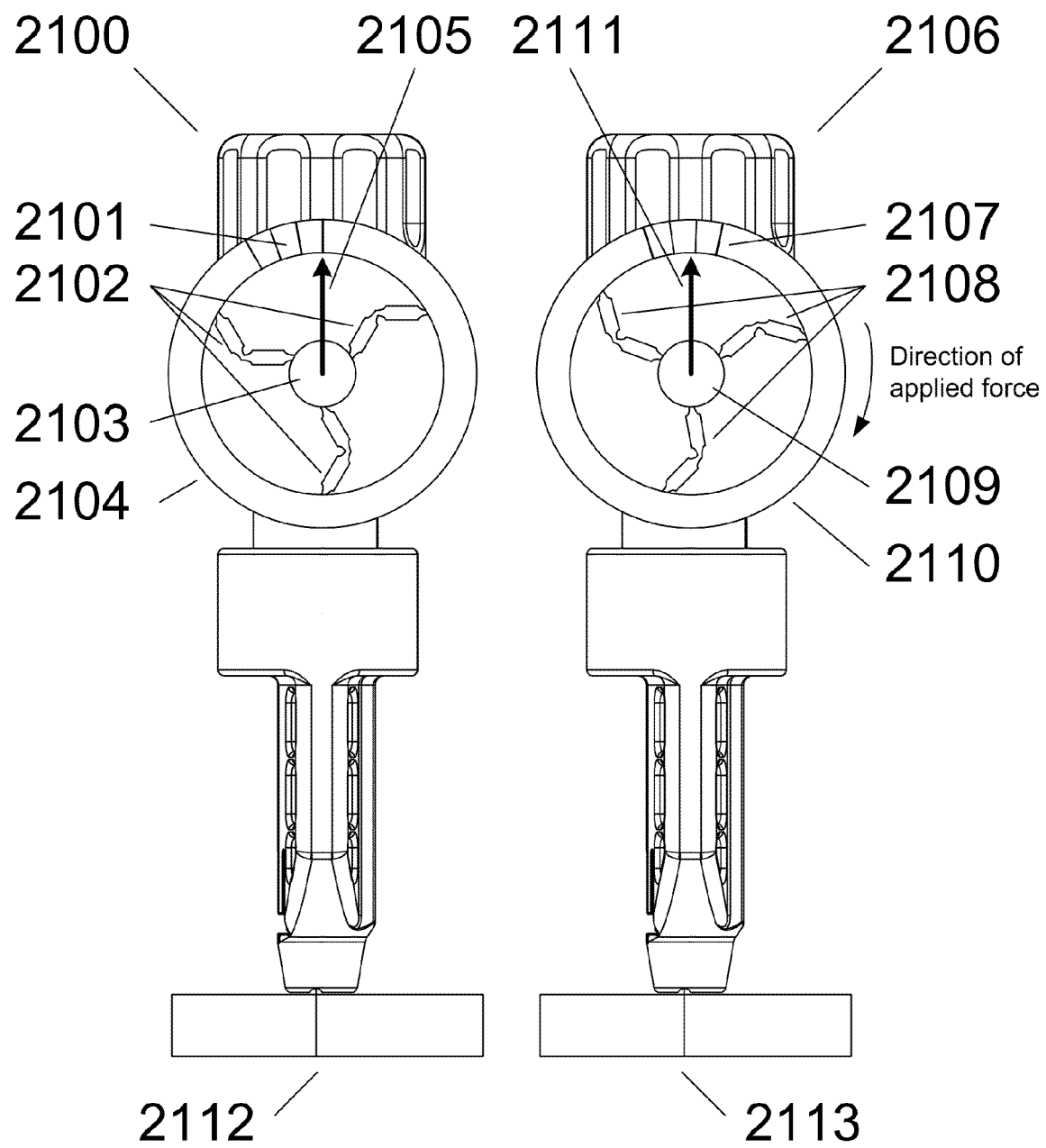
FIG. 21 shows an embodiment of a medical device comprising a mechanism to provide an indication of force being applied to flexible sutures.

FIG. 21 shows an embodiment of a medical device comprising a mechanism to provide an indication of force being applied to a flexible suture being tensioned by the medical device. Medical device 2100 is shown having no force applied to tensioning handle 2104. Medical device 2106 is shown with force applied to tensioning handle 2110.

Tensioning handle 2104, 2110 is preferably connected to tensioning shaft 2103, 2109 by flexures 2102, 2108. Dial 2101, 2107 may be attached to or marked on tensioning handle 2104, 2110. Dial 2101, 2107 may be a series of grooves, numbers, or other markings. Needle indicator 2105, 2111 is preferably rigidly attached to tensioning shaft 2103, 2109 and points to dial 2101, 2107.

Flexures 2102, 2108 may bend at the middle and the points that they are connected to tensioning handle 2104, 2110 and tensioning shaft 2103, 2109. Increasing the force that is applied to tensioning handle 2104, 2110 increases the amount that flexures 2102, 2108 bend from their rest position. Flexures 2102 are shown with no force being applied to tensioning handle 2104, and flexures 2108 are shown with some force being applied to tensioning handle 2110. As flexures 2102, 2108 are bent, tensioning handle 2104, 2110 rotates about tensioning shaft 2103, 2109, changing the position on dial 2101, 2107 that is pointed to by needle indicator 2105, 2111. The position that needle indicator 2105, 2111 points to on dial 2101, 2107 provides an indication of the force that is being delivered to tension shaft 2103, 2109. Providing an indication of the force that is being delivered to tension shaft 2103, 2109 is useful to inform the medical device user of the quantity of tension being applied to flexible sutures 2112, 2113.

Figure 22:
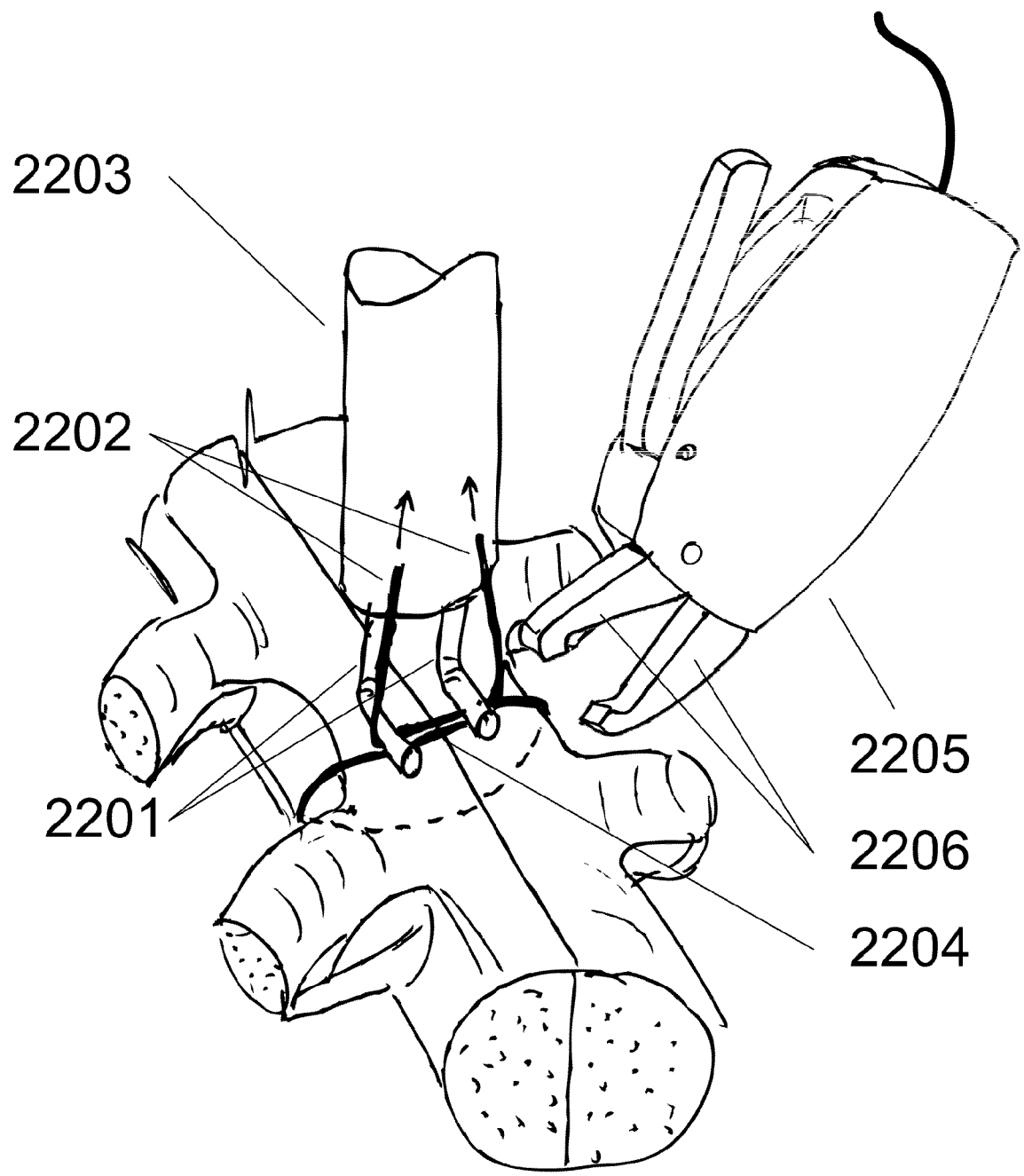
FIG. 22 is a diagram of an embodiment of a medical device that uses spot welding to bond wires.

An alternative to securing the wires by twisting is using a form of welding, such as spot welding (also referred to as "resistance welding") to permanently bond flexible sutures made of wire together after tensioning. FIG. 22 is a diagram of an embodiment of a medical device that uses spot welding to bond wires. This base 2203 of this tool comprises two tensioning posts 2201 separated sufficiently to allow a welding tool to fit in between the tensioning posts 2201. Ends of wire suture 2202 may be tensioned using an embodiment disclosed previously, such as with a tensioning shaft and tensioning handle, or may be tensioned using one of many other common tensioning methods available. After wire suture 2202 is properly tensioned, spot welder 2205 is used to bond the wires in bonding region 2204. Spot welder 2205 grips the wires in the bonding region 2204 with electrodes 2206 and applies current to bond the wires. The use of spot welding for securing wires is well known in the art of dentistry and does not require elaboration. One of many dental wire spot welder suppliers is Dentaurum (www.dentaurum.de).

Some units are available in the shape of pliers, making it possible to access the limited space under the tensioning tool. Such spot welding pliers are disclosed in U.S. Pat. No. 2,267,297 hereby incorporated by reference. It was found that a setting of about 1-2 VAC is sufficient for welding the 0.8 mm type 316L stainless steel wire used for sternal closure. A voltage of about 1-2 VAC corresponds to a current of about 1000-2000 A across the wire. Pulse duration is 10-20 mS. Shorter pulses are less desirable as higher voltages are required to deliver the same energy. Because of the very low voltage and because an AC voltage is used, the muscles do not respond to the voltage, particularly if a frequency of above 1 KHz is chosen. Since most modern inverters operate above 20 KHz, no biological response will occur.

Major advantages of securing wires by welding include the very low profile of the finished joint (after clipping off excess wire) and high tension retention.

What is claimed is:

1. A medical instrument comprising:
   a base comprising a bone contacting surface that in use contacts at least one bone;
   a first device, at least part of the first device movable with respect to the base to tension at least one flexible suture extending around at least a portion of the at least one bone, and
   a second device physically mounted to the base and comprising a flexible suture retaining structure arranged to retain at least a portion of the at least one flexible suture, at least a part of the second device rotatable with respect to the base to apply a plurality of twists to the at least one flexible suture to encircle at least the portion of the at least one bone with the at least one flexible suture when the at least part of the second device is rotated with respect to the base, and
   wherein the base comprises a threaded portion and an open slot, the open slot arranged to intercept the bone contacting surface, and the open slot of the base extends through the threaded portion of the base, and wherein the second device comprises a threaded portion threadedly coupled to the threaded portion of the base, the threaded portion of the second device including a respective open slot extending therethrough, the respective open slots of the base and the second device each of which only partially surround the at least one flexible suture during use.

2. The medical instrument of claim 1 wherein the open slot of the base extends continuously from a location where the at least one flexible suture exits the base to a location where the second device is physically mounted to the base.

3. The medical instrument of claim 1 wherein the first device is physically mounted to the second device.

4. A medical instrument comprising:
   a support;
   a first device operable to apply tension to at least one flexible suture extending around at least a portion of at least one bone,
   a second device, at least a part of the second device rotatably mounted to the support to rotate with respect thereto to apply a plurality of twists to the at least one flexible suture to encircle at least the portion of the at least one bone with the at least one flexible suture when the at least part of the second device is rotated with respect to the support; and
   a third device arranged to reduce the tension applied to the at least one flexible suture as the plurality of twists are applied to the at least one flexible suture, and wherein the at least one flexible suture is a metal wire suture; and
   a flexible suture retaining structure arranged to retain a portion of the at least one flexible suture by the medical instrument, wherein a distance between a location of the flexible suture retaining structure where the portion of the at least one flexible suture is retained and a location where the at least one flexible suture exits the support decreases when the at least a part of the second device is rotated with respect to the support.

5. The medical instrument of claim 4 wherein the at least a part of the second device is threadedly coupled to the support.

6. The medical instrument of claim 4 wherein the second device comprises a twisting head in which the at least one flexible suture is retained, the twisting head rotatable in use with respect to the support while the flexible sutures are retained therein.

7. The medical instrument of claim 4 wherein the second device comprises a twisting head rotatably mounted to the support for rotation with respect thereto about a first axis and a torsion shaft comprising the flexible suture retaining structure, the torsion shaft rotatably mounted to the twisting head to rotate with respect thereto about a second axis, the second axis non-parallel to the first axis.

8. The medical instrument of claim 4, further comprising at least a first spring and a second spring, the second spring oppositely wound to at least the first spring.

9. The medical instrument of claim 4 wherein the support comprises a first threaded portion and the second device comprises a second threaded portion threadedly coupled to the first threaded portion of the support, the first and the second threaded portions each including a respective open slot extending therethrough, the respective open slots of the first and second threaded portions each of which only partially surround the at least one flexible suture during use.

10. The medical surgical instrument of claim 4 wherein a torsion spring physically couples a handle to the flexible suture retaining structure to cause the flexible suture retaining structure to wind up the at least one flexible suture in response to a rotation of the handle.

11. A medical instrument comprising:
    a support;
    a first device operable to apply tension to at least one flexible suture extending around at least a portion of at least one bone,
    a second device, at least a part of the second device rotatably mounted to the support to rotate with respect thereto to apply a plurality of twists to the at least one flexible suture to encircle at least the portion of the at least one bone with the at least one flexible suture when the at least part of the second device is rotated with respect to the support;
    a third device arranged to reduce the tension applied to the at least one flexible suture as the plurality of twists are applied to the at least one flexible suture, and wherein the at least one flexible suture is a metal wire suture; and
    wherein the third device comprises an elastic member arranged to be tensioned when the first device is operated to apply tension to the at least one flexible suture extending around the at least a portion of the at least one bone and arranged to be untensioned when at least the part of the second device is rotated with respect to the support.

12. A medical instrument, comprising:
    a base comprising a bone contacting surface that in use contacts at least one bone and does not move relative to the base;

a first device, at least part of the first device movable with respect to the base to tension at least one flexible suture extending around at least a portion of the at least one bone, and a second device physically mounted to the base and comprising a flexible suture retaining structure arranged to retain at least a portion of the at least one flexible suture, at least a part of the second device rotatable with respect to the base to apply a plurality of twists to the at least one flexible suture to encircle at least the portion of the at least one bone with the at least one flexible suture, wherein the second device comprises a threaded portion threadedly coupled to the base and the at least part of the second device comprises a twisting head rotatably mounted to the base via the threaded portion to rotate with respect to the base about a first axis, and the flexible suture retaining structure comprises a torsion shaft rotatably mounted to the twisting head to rotate with respect thereto about a second axis, the second axis non-parallel to the first axis.

13. A medical instrument, comprising:

a base comprising a bone contacting surface that in use contacts at least one bone and does not move relative to the base;

a first device, at least part of the first device movable with respect to the base to tension at least one flexible suture extending around at least a portion of the at least one bone, and a second device physically mounted to the base and comprising a flexible suture retaining structure arranged to retain at least a portion of the at least one flexible suture, at least a part of the second device rotatable with respect to the base to apply a plurality of twists to the at least one flexible suture to encircle at least the portion of the at least one bone with the at least one flexible suture, wherein the second device comprises a threaded portion threadedly coupled to the base and the at least a part of the second device comprises a twisting head rotatably mounted to the base via the threaded portion to rotate with respect to the base, and the at least part of the first device comprises a torsion shaft rotatably mounted to the twisting head.

14. The medical instrument of claim 13, further comprising: a one-way clutch and wherein the at least a part of the first device comprises a handle physically coupled to the torsion shaft and the one-way clutch.

15. The medical instrument of claim 14 wherein the one-way clutch comprises a clutch spring physically coupled between the handle and the twisting head to restrict rotation of the handle to a single rotational direction.

16. The medical instrument of claim 13, further comprising: a torsion spring arranged to physically couple the handle to the torsion shaft and which transfers a rotation of the handle into a rotation of the torsion shaft.

17. A medical instrument, comprising:

a base comprising a bone contacting surface that in use contacts at least one bone;

a first device, at least part of the first device movable with respect to the base to tension at least one flexible suture extending around at least a portion of the at least one bone, a second device physically mounted to the base and comprising a flexible suture retaining structure arranged to retain at least a portion of the at least one flexible suture, at least a part of the second device rotatable with respect to the base to apply a plurality of twists to the at least one flexible suture to encircle at least the portion of the at least one bone with the at least one flexible suture; and a spring arranged to provide an increasing amount of spring force when the at least a part of the first device is moved with respect to the base and to provide a decreasing amount of spring force when the at least part of the second device is rotated with respect to the base to apply the plurality of twists to the at least one flexible suture to encircle at least the portion of the at least one bone with the at least one flexible suture.

18. A medical instrument, comprising:

a base comprising a bone contacting surface that in use contacts at least one bone;

a first device, at least part of the first device movable with respect to the base to tension at least one flexible suture extending around at least a portion of the at least one bone, a second device physically mounted to the base and comprising a flexible suture retaining structure arranged to retain at least a portion of the at least one flexible suture, at least a part of the second device rotatable with respect to the base to apply a plurality of twists to the at least one flexible suture to encircle at least the portion of the at least one bone with the at least one flexible suture; and a spring arranged to increase force applied to the at least one flexible suture when the at least a part of the first device is moved with respect to the base to increase tension in the at least one flexible suture and to reduce the force applied to the at least on flexible suture when the at least a part of the second device is rotated with respect to the base to apply the plurality of twists to the at least one flexible suture to encircle at least the portion of the at least one bone with the at least one flexible suture.

19. A medical instrument, comprising:

a base comprising a bone contacting surface that in use contacts at least one bone;

first means for applying tension to at least one flexible suture extending around at least a portion of the at least one bone when the first means is moved with respect to the base wherein the at least one flexible suture is a metal wire suture;

second means for applying a plurality of twists to the at least one flexible suture to encircle at least the portion of the at least one bone with the at least one flexible suture when the second means for applying a plurality of twists to the at least one flexible suture is rotated with respect to the base, wherein each of the first means for applying tension to at least one flexible suture and the second means for applying a plurality of twists to the at least one flexible structure is movably coupled to the base; and third means for reducing the tension applied to the at least one flexible suture as the plurality of twists are applied to the at least one flexible suture, and where the second means for applying a plurality of twists to the at least one flexible suture comprises a flexible suture retaining structure to retain the at least one flexible suture and the third means for reducing the tension applied to the at least one flexible suture varies a distance between a location where the at least one flexible suture exits the base and a location where the at least one flexible suture is retained by the flexible suture retaining structure.

20. A medical instrument, comprising:
a support;
a first device operable to apply tension to at least one flexible suture extending around at least a portion of at least one bone,
a second device, at least a part of the second device rotatably mounted to the support to rotate with respect thereto to apply a plurality of twists to the at least one flexible suture to encircle at least the portion of the at least one bone with the at least one flexible suture; and
a third device arranged to reduce the tension applied to the at least one flexible suture as the plurality of twists are applied to the at least one flexible suture;
a flexible suture retaining structure arranged to retain a portion of the at least one flexible suture by the medical instrument, wherein a distance between a location of the flexible suture retaining structure where the portion of the at least one flexible suture is retained and a location where the at least one flexible suture exits the support is varied when the third device reduces the tension applied to the at least one flexible suture as the plurality of twists are applied to the at least one flexible suture.

21. A medical instrument to secure at least one flexible suture to at least one body part, the medical instrument comprising:
a base;
a twisting head rotatably coupled to the base to rotate with respect thereto to secure portions of the at least one flexible suture together;
a flexible suture retaining structure in which the at least one flexible suture is retained, the flexible retaining structure movably coupled to the twisting head; and
a tension decreasing device arranged to apply a decreasing tension to the at least one flexible suture during the securing of the portions of the at least one flexible suture together, and wherein the tension decreasing device varies a distance between a location where the at least one flexible suture exits the base and a location of the flexible suture retaining structure.

22. A medical instrument to secure at least one flexible suture to at least one body part, the medical instrument comprising:
a base;
a twisting head rotatably coupled to the base to rotate with respect thereto to secure portions of the at least one flexible suture together;
a flexible suture retaining structure in which the at least one flexible suture is retained, the flexible retaining structure movably coupled to the twisting head; and
a tension decreasing device arranged to apply a decreasing tension to the at least one flexible suture during the securing of the portions of the at least one flexible suture together, and wherein the tension decreasing device comprises a threaded portion of the twisting head and a threaded portion of the base, the threaded portion of the twisting head threadedly engaging the threaded portion of the base to vary a distance between the flexible retaining structure and a location where the at least one flexible suture exits the base in response to rotation of the twisting head relative to the base.

23. The medical instrument of claim 22, further comprising:
a torsion spring physically coupled to the flexible suture retaining structure to wind up the at least one flexible suture in response to the distance between the flexible suture retaining structure and the location where the at least one flexible suture exits the base decreasing in response to rotation of the twisting head relative to the base.

24. A medical instrument to secure at least one flexible suture to at least one body part, the medical device comprising:
a base;
a twisting head, the twisting head rotatably mounted to the base to rotate with respect thereto about a first axis to secure portions of the at least one flexible suture together;
a torsion shaft having a flexible suture retaining structure arranged to retain a portion of the at least one flexible suture, the torsion shaft rotatably mounted to the twisting head to rotate with respect thereto about a second axis to apply tension to the at least one flexible suture, the second axis non-parallel to the first axis; and
a handle selectively moveable by a user,
wherein a distance between a location of the flexible suture retaining structure where the portion of the at least one flexible suture is retained and a location where the at least one flexible suture exits the base decreases when the twisting head is rotated with respect to the base.

25. The medical instrument of claim 24, further comprising a one-way clutch spring, the one-way clutch spring physically coupled to limit rotation of the handle to a single rotational direction.

26. The medical instrument of claim 24, further comprising a first torsion spring which transfers a rotation of the handle into a rotation of the torsion shaft and a second torsion spring, the second torsion spring oppositely wound to the first torsion spring.

27. The medical instrument of claim 24, further comprising a device arranged to apply a decreasing tension to the at least one flexible suture while the twisting head is rotated with respect to the base.

28. A medical instrument comprising:
a base comprising a bone contacting surface that in use contacts at least one bone;
a first device, at least part of the first device movable with respect to the base to tension at least one flexible suture extending around at least a portion of the at least one bone,
a second device physically mounted to the base and comprising a flexible suture retaining structure arranged to retain at least a portion of the at least one flexible suture, at least a part of the second device rotatable with respect to the base to apply a plurality of twists to the at least one flexible suture to encircle at least the portion of the at least one bone with the at least one flexible suture; and
a flexible suture retaining structure arranged to retain a portion of the at least one flexible suture by the medical instrument, wherein a distance between a location of the flexible suture retaining structure where the portion of the at least one flexible suture is retained and a location where the at least one flexible suture exits the base decreases when the at least a part of the second device is rotated with respect to the base.

29. A medical surgical instrument comprising:
a support;
a first device operable to apply tension to at least one flexible suture extending around at least a portion of at least one bone,
a second device, at least a part of the second device rotatably mounted to the support to rotate with respect thereto to apply a plurality of twists to the at least one flexible suture to encircle at least the portion of the at least one bone with the at least one flexible suture when the at least part of the second device is rotated with respect to the support; and a third device arranged to reduce the tension applied to the at least one flexible suture as the plurality of twists are applied to the at least one flexible suture, and wherein the at least one flexible suture is a metal wire suture; and a torsion spring is physically coupled to the flexible suture retaining structure to cause the flexible suture retaining structure to further wind up the at least one flexible suture in response to a distance between a location of the flexible suture retaining structure where the portion of the at least one flexible suture is retained and a location where the at least one flexible suture exits the support decreasing when the at least a part of the second device is rotated with respect to the support.

* * * * *